United States Patent
Spaulding et al.

(12)

(10) Patent No.: US 10,709,654 B2
(45) Date of Patent: Jul. 14, 2020

(54) SYNERGISTIC PHOTOPROTECTIVE COMPOSITIONS

(71) Applicant: EDGEWELL PERSONAL CARE BRANDS, LLC, Chesterfield, MO (US)

(72) Inventors: Laura Spaulding, Wayne, NJ (US); James SaNogueira, Wesley Hills, NY (US); Geng Li, Brooklyn, NY (US)

(73) Assignee: EDGEWELL PERSONAL CARE BRANDS, LLC, Chesterfield, MO (US)

( * ) Notice: Subject to any disclaimer, the term of this patent is extended or adjusted under 35 U.S.C. 154(b) by 248 days.

(21) Appl. No.: 14/230,167

(22) Filed: Mar. 31, 2014

(65) Prior Publication Data

US 2017/0189293 A1    Jul. 6, 2017

Related U.S. Application Data

(60) Provisional application No. 61/807,077, filed on Apr. 1, 2013.

(51) Int. Cl.

| | |
|---|---|
| *A61K 8/26* | (2006.01) |
| *A61K 8/28* | (2006.01) |
| *A61K 8/29* | (2006.01) |
| *A61K 8/35* | (2006.01) |
| *A61K 8/40* | (2006.01) |
| *A61K 8/58* | (2006.01) |
| *A61K 8/85* | (2006.01) |
| *A61K 8/891* | (2006.01) |
| *A61K 8/894* | (2006.01) |
| *A61Q 17/04* | (2006.01) |

(52) U.S. Cl.
CPC .............. *A61K 8/585* (2013.01); *A61K 8/26* (2013.01); *A61K 8/28* (2013.01); *A61K 8/29* (2013.01); *A61K 8/35* (2013.01); *A61K 8/40* (2013.01); *A61K 8/85* (2013.01); *A61K 8/891* (2013.01); *A61K 8/894* (2013.01); *A61Q 17/04* (2013.01); *A61K 2800/594* (2013.01)

(58) Field of Classification Search
CPC ...... A61K 8/35; A61K 2800/594; A61K 8/29; A61K 8/40; A61K 8/585; A61K 8/26; A61K 8/28; A61K 8/85; A61K 8/891; A61K 8/894; A61Q 17/04
See application file for complete search history.

(56) References Cited

U.S. PATENT DOCUMENTS

| | | | | |
|---|---|---|---|---|
| 4,686,099 | A * | 8/1987 | Palinczar | A61K 8/731 424/47 |
| 2003/0198655 | A1* | 10/2003 | Kaneda | A61K 8/06 424/401 |
| 2005/0002994 | A1* | 1/2005 | Goppel | A61K 8/0208 424/443 |
| 2005/0053561 | A1 | 3/2005 | Suginaka | |
| 2007/0166247 | A1 | 7/2007 | Alianao et al. | |
| 2007/0231287 | A1 | 10/2007 | Lu | |
| 2008/0193405 | A1 | 8/2008 | Mukherjee et al. | |
| 2009/0035234 | A1* | 2/2009 | Cunningham | A61K 8/046 424/59 |
| 2010/0092410 | A1* | 4/2010 | Cockerell | A61K 8/27 424/59 |
| 2011/0064680 | A1* | 3/2011 | Davies | A61K 8/35 424/59 |
| 2012/0014882 | A1* | 1/2012 | Singleton | A61K 8/34 424/45 |

OTHER PUBLICATIONS

COSMOSURF PG 1-IS, Developmental Technical Data Sheet, SurfaTech Corporation, 2012, pp. 1-9. (Year: 2012).*
Pupa Luminys Touch Face Illuminator.
International preliminary report on patentability issued in connection with corresponding PCT Application No. PCT/US2014/032323 dated Oct. 6, 2015.
Written opinion issued in connection with corresponding PCT Application No. PCT/US2014/032323 dated Sep. 30, 2015.
Search report issued in connection with corresponding PCT Application No. PCT/US2014/032323 dated Jul. 31, 2014.
Canada Office Action issued in connection with corresponding CA Application No. 2911686 dated Nov. 21, 2019.
European Office Action issued in connection with corresponding EP Application No. 14724242.4 dated Sep. 6, 2016.
Australian First Office Action issued in connection with corresponding AU Application No. 2014251296 dated Jan. 24, 2018.
Australian Second Office Action issued in connection with corresponding AU Application No. 2014251296 dated Jan. 2, 2019.

* cited by examiner

*Primary Examiner* — Michael B. Pallay

(57) ABSTRACT

A photoprotective composition can be utilized for a variety of cosmetic compositions. A photoprotective composition comprises one or more photoactive agents, and a synergistic combination of polymers. The photoprotective composition can provide a substantially a complete film. The photoprotective composition may comprise an alkyl dimethicone, a polymer with ester linkages, and a phenyl silicone or stearate. The photoprotective composition can further comprise abietic acid and ester derivatives. The photoprotective composition can be a liquid such that it is easily and consistently dispensed from a bottle, pump or spray.

18 Claims, 11 Drawing Sheets

(10 of 11 Drawing Sheet(s) Filed in Color)

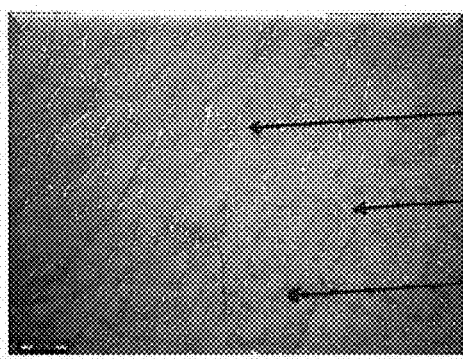 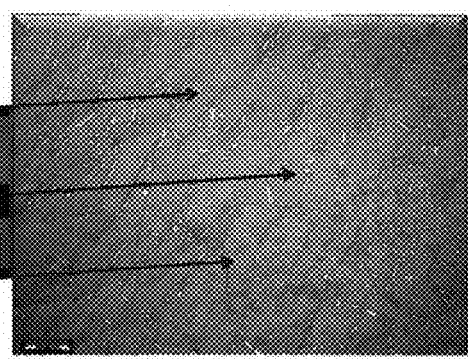
FIG. 7B                    FIG. 7C

SYNERGISTIC PHOTOPROTECTIVE COMPOSITIONS

CROSS REFERENCE TO RELATED APPLICATION

This application claims priority under 35 U.S.C. § 119(e) of U.S. Provisional Patent Application No. 61/807,077, filed on Apr. 1, 2013, the disclosure of which is hereby incorporated by reference in its entirety.

BACKGROUND OF THE INVENTION

A. Field of Endeavor

The present invention relates to photoprotective compositions with improved absorbance and film forming abilities.

B. Background Information

Outdoor daytime activities such as swimming, fishing, exercising, landscaping, construction, children playing, etc., can expose the dermis of people participating in these activities to the damaging effects of ultraviolet (UV) exposure from both UVA and UVB radiation from the sun. Long term health effects are associated with early incidences of sunburn, and therefore, early use of photo-protective products should be encouraged for both young and older generations. Sunscreens are applied to the skin to protect the skin from the sun's ultraviolet rays that can lead to erythema (sunburn).

Sunlight or ultraviolet radiation in the UVB range has a wavelength of 290 nanometers to 320 nanometers and is known to be the primary cause of sunburn. Ultraviolet rays at a wavelength of 320 nanometers to 400 nanometers, known as UVA radiation, can cause tanning of the skin. However, in the process of doing so, the UVA rays can damage or harm the skin. UVA and UVB rays are known as ultraviolet radiation (UVR).

Aside from the immediate malady of sunburn, excessive sunlight exposure can lead to other skin disorders. For instance, prolonged exposure to the sun may lead to actinic keratosis and carcinomas. Another long-term effect of sun exposure is premature aging of the skin. This condition is characterized by skin that is wrinkled, cracked and has lost its elasticity.

It is known that the combination of organic: active ingredients providing broad spectrum photoprotection according to the 2011 United States Food and Drug Administration ("FDA") Final Rule for Very Water Resistance can provide broad spectrum coverage. There is always a need for providing better broad spectrum coverage and/or UV absorbance, Unfortunately, doing so with only the approved active ingredients in the approved ranges can prove difficult and furthermore, it can be expensive. As such, there is a need for lower cost alternatives that yield improved broad spectrum coverage and/or UV absorbance, or, in the alternative, are able to obtain the same broad spectrum coverage at a lower cost.

In addition to improved broad spectrum coverage and/or UV absorbance, there is a further need to provide for photoprotective compositions that form substantially better films and films that are substantially more durable. As one skilled in the art understands, a photoprotective composition can provide broad spectrum coverage and/or UV absorbance initially, but it will be moot if it cannot provide complete coverage by virtue of poor film formation. Film formation is significant in at least two ways (a) substantially complete and uniform film formation, and (b) maintaining the film over a period of time and through a plurality of elements/factors/disruptors.

Additionally, there is no clear and/or homogenous and/or anhydrous and/or alcohol free photoprotective composition that utilizes global regulatory body approved active agents that furthermore, are both mild to both ocular and dermal regions of the body. Aerosol and bag on valve ("BOV") spray-type lotions are, growing segment in the photoprotection marketplace due to dispensing convenience and more effective coverage of hard to reach areas when self-applying photoprotection product. The only Tear Free/Sting Free photoprotective aerosol or BOV product available to the consumer is an opaque, water-based lotion spray that needs to be shaken before use, and the liquid sprays on as an unsightly white film on wet or dry skin.

SUMMARY

The present disclosure provides a photoprotective composition comprising at least one photoactive agent, and a synergistic combination of polymers. The photoprotective composition with the synergistic combination of polymers provides for a substantially complete film, an improved film formation, increased uniformity in film formation, increased film durability, increased total UVA and/or UVB absorbance, increased UVR absorbance, increased broad spectrum coverage, increased breadth of broad spectrum coverage, increased magnitude in broad spectrum coverage, water resistance, and combinations thereof.

In one embodiment of the present disclosure, the one or more photoactive agents are present in an amount about 0.1 wt. % to about 40 wt. %, based on the total weight of the composition.

The synergistic combination of polymers can comprise an alkyl dimethicone, a polymer with ester linkages, and a phenyl silicone or a styrene. In one embodiment, the synergistic combination of polymers is present in an amount of 0.1% to about 15%. In another embodiment, the alkyl dimethicone is present in an amount of about 0.1% to about 5%, and preferably in a range of about 0.1% to 1.5%. In another embodiment, the polymer with ester linkages is present in an amount of about 0.1% to about 5%, and preferably in an amount of about 0.1% to about 1.5%. In another embodiment, the phenyl silicone or the styrene is present in an amount of about 0.1% to about 5%, and preferably in a range of about 0.1% to about 1.5%.

In another embodiment, the photoprotective composition can also comprise an abietic acid and ester derivatives. In one embodiment, the abietic acid and ester derivatives is present in an amount of about 0.1% to about 5%, and preferably between about 0.1% to about 1.5%.

The present disclosure provides for a photoprotective composition that provides any or all of the following characteristics, including without limitation: is a single phase, is homogenous, is substantially non-whitening, is substantially non-irritating, is anhydrous, is water-resistant, is a skin-protectant, is substantially free of preservatives, is substantially free of surfactants, is substantially free of alcohol, is substantially free of emulsifiers, is substantially free of silicon, and any combinations thereof. The compositions are in the form of a flowing liquid that can be dispensed from a bottle with a suitable closure, or in a spray format such as an aerosol or pump spray.

In one aspect of the present disclosure, the photoprotective composition is a single-phase. In other words, the photoprotective composition does not have separate phases that could comprise without limitation, a water phase, an emulsion phase, and/or an oil phase.

In another aspect of the present disclosure, the photoprotective composition is homogenous. In other words, the product does not require, shaking, agitation, or other physical movement in order to dispense the photoprotective composition from a container such that the photoprotective composition is of a substantially uniform consistency.

In another aspect of the present disclosure, the photoprotective composition is substantially non-whitening. In other words, the photoprotective composition is sufficiently translucent, transparent, clear, or any other adjective that describes a colorless or see-through substance. As hereinafter used, the term "non-whitening" is defined to include without limitation the aforementioned adjectives, such as, i.e., translucent, transparent, clear, colorless or see-through. The photoprotective composition is substantially non-whitening upon being dispensed from a container such that the photoprotective composition is substantially non-whitening when applied to a substrate, topically, to the dermis or skin, or any other surface. As hereinafter used, the terms "substrate", "topical", "dermis", "skin" and any other term referring to a surface on which a photoactive agent is applied, are all interchangeable. The photoprotective composition may also be substantially non-whitening after being topically applied and having sufficient time to dry. The photoprotective composition may also be substantially non-whitening when applied to substantially wet or substantially dry substrates, or combinations thereof.

In another aspect of the present disclosure, the photoprotective composition is anhydrous.

In another aspect of the present disclosure, the photoprotective composition is water-resistant. The photoprotective composition may be suitable for sustaining water-resistance for at least forty (40) minutes. The photoprotective composition may be suitable for sustaining water-resistance for at least eighty (80) minutes. In any event, the photoprotective composition may be suitable to sustain a suitable level of photoprotection, such as but not limited to photoprotection achieving an SPF of 15, 30, 50 and/or 50+, as demonstrated by any or all of the FDA critical wavelength method, the UVAPF method, and the ISO24443 method, the AMA Australian/New Zealand water resistance test method, for a period of forty (40), and/or eighty (80) minutes and/or additionally, four (4) hours.

In another aspect of the present disclosure, the photoprotective composition is a skin-protectant.

In another aspect of the present disclosure, the photoprotective composition is able to achieve one or more of the aforementioned characteristics without resorting to other chemicals or substances. For instance, in one embodiment of the present disclosure, the photoprotective composition does not contain preservatives. In other words, the photoprotective composition of the present disclosure can be substantially free of preservatives or preservative-free. That isn't to say that the present disclosure's photoprotective composition cannot include preservatives; it is to say, however, that the photoprotective composition of the present disclosure does not require preservatives.

In another aspect of the present disclosure, one embodiment of the photoprotective composition does not contain surfactants. In other words, the photoprotective composition of the present disclosure can be substantially free of surfactants or surfactant-free. That isn't to say that the present disclosure's photoprotective composition cannot include surfactants; it is to say, however, that the photoprotective composition of the present disclosure does not require surfactants.

In another aspect of the present disclosure, one embodiment of the photoprotective composition does not contain alcohol. In other words, the photoprotective composition of the present disclosure can be substantially free of alcohol or alcohol-free. That isn't to say that the present disclosure's photoprotective composition cannot include alcohols; it is to say, however, that the photoprotective composition of the present disclosure does not require alcohols.

In another aspect of the present disclosure, one embodiment of the photoprotective composition does not contain emulsifiers. In other words, the photoprotective composition of the present disclosure can be substantially free of emulsifiers or emulsifier-free. That isn't to say that the present disclosure's photoprotective composition cannot include emulsifiers; it is to say, however, that the photoprotective composition of the present disclosure does not require emulsifiers.

In another aspect of the present disclosure, one embodiment of the photoprotective composition does not contain silicone. In other words, the photoprotective composition of the present disclosure can be substantially free of silicone or silicone-free. That isn't to say that the present disclosure's photoprotective composition cannot include silicone; it is to say, however, that the photoprotective composition of the present disclosure does not require silicone.

BRIEF DESCRIPTION OF THE SEVERAL VIEWS OF THE DRAWINGS

The specification contains at least one color photograph. Copies of this patent/patent application publication with color photograph(s) will be provided by the Office upon request and payment of the necessary fee.

FIG. 7B is an image of film formation of a photoprotective composition

FIG. 7C is an image of film formation of a photoprotective composition

DETAILED DESCRIPTION OF THE INVENTION

Figure 1:
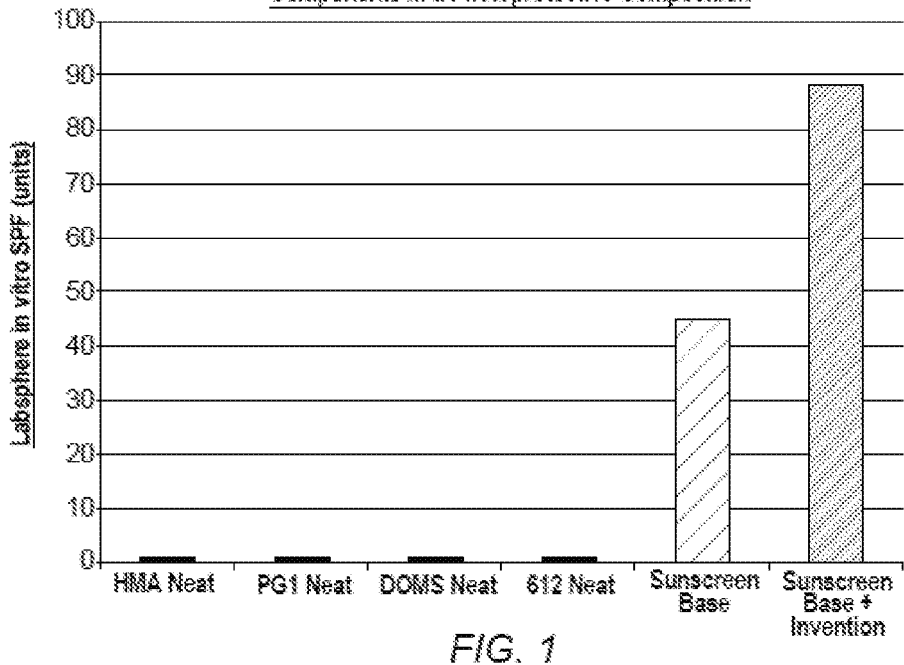
FIG. 1 is a chart showing in vitro SPF of photoprotective compositions

The present disclosure will be discussed hereinafter in detail in terms of the preferred embodiments according to the present disclosure with reference to the accompanying drawings. In the following description, numerous, specific details are set forth in order to provide a thorough understanding of the present disclosure. It will be obvious, however, to those skilled in the art that the present disclosure may be practiced without these specific details. In other instances, well-known structures are not shown in detail in order to avoid unnecessary obscurity of the present disclosure.

The term "cosmetic composition" may include, but is not limited to, the following: sunscreens, dermatological compositions, make-up compositions, make-up removers, cleansers, lotions, gels, creams, sticks, balms, lip balms, powders, milks, conditioners, sprays, eye-liners, solutions, or serums. One of skill in the art understands that the photoprotective compositions of the present disclosure can facilitate cosmetic compositions.

The present disclosure provides for embodiments of photoprotective compositions comprising at least one photoactive agent and a synergistic combination of polymers. The synergistic polymer system comprises an alkyl dimethicone, a polymer with ester linkages, and a phenyl silicone or a styrene. In one embodiment, the synergistic combination of polymers is present in an amount of about 0.1% to about 15%. In another embodiment, the alkyl dimethicone is present in an amount of about 0.1% to about 5%, and preferably in an amount of about 0.1% to about 1.5%. In another embodiment, the polymer with ester linkages is present in an amount of about 0.1% to about 5%, and preferably in an amount of about 0.1% to about 1.5%. In another embodiment, the phenyl silicone or the styrene is present in an amount of about 0.1% to about 5%, and preferably in a range of about 0.1% to about 1.5%.

In one embodiment, the one or more photoactive agents comprises, such as but without limitation, i.e., p-aminobenzoic acid (PABA) and derivatives thereof, butyl methoxydibenzoylmethane, benzophenones, hydroxy-substituted benzophenones, methoxy-substituted benzophenones, benzophonone-1, benzophenone-2, benzophenone-3, benzophenone-4, benzophenone-6, benzophenone-8, benzophenone-12, methoxycinnamate, ethyl dihydroxypropyl-p-aminobenzoate, glyceryl-p-aminobenzoate, homosalate, methyl anthranilate, octocrylene, octyl dimethyl-p-aminobenzoate, octyl methoxycinnamate, octyl salicylate, 2 phenylbenzimidazole-5-sulphonic acid, triethanolamine salicylate, 3-(4-methylbenzylidene)-camphor, red petrolatum,3-(4-methylbenzyldine)boran-2-one (methylbenzindinecamphor), benzotriazole, salicylates, phenylbenzimidazole-5-sulfonic acid, methylene bis-benzotriazolyl tetramethylbutyl phenol, avobenzone, 4-isopropyldibenzoymethane, butylmethoxydibenzoylmethane, octocrylene, octisalate, oxybenzone, bis-ethylhexyloxyphenol methoxy triazine, 4-isopropyl-dibenzoylmethane, metal oxides, zinc oxide, octyltriethoxy silanol, titanium dioxide, alumina, triethoxy silane, and any combinations thereof.

In one embodiment, the one or more active agents are present in an amount about 0.1 wt. % to about 40 wt. %, based on the total weight of the photoprotective composition. In another embodiment, the one or more photoactive agents comprises: homosalate (trade name PARSOL® HMS) in amount less than or equal to about 15 wt. %, octisalate (trade name PARSOL® EHS) in an amount less than or equal to about 5 wt. %, octocrylene (trade name PARSOL® 340) in an amount less than or equal to about 10 wt. %, avobenzone (PARSOL® 1789) in an amount less than or equal to about 5 wt. %, oxybenzone (trade name ESCALOL® 567) in an amount less than or equal to about 0.5 wt. %, bis-ethylhexyloxyphenol methoxyphenyl triazine (bemotrizinol) (trade name TINOSORB® S) in an amount less than or equal to about 2.0 wt. %, zinc oxide and octyltriethoxy silanol (trade name ZANO® 10 Plus) in an amount of less than or equal to about 10 wt. %, and titanium dioxide and alumina and triethoxysilane (UV TITAN® 765) in an amount of less than or equal to about 5 wt. %, based on the total weight of the photoprotective composition. In yet another embodiment, the photoprotective composition may be sufficient with only one or two or three photoactive agents. For instance, in one embodiment, oxybenzone is not needed in order to provide a photoprotective composition.

In another embodiment, the alkyl dimethicone comprises, such as but without limitation, i.e., alkyl dimethicones with a hydrophilic group, alkyl-PPG dimethicones, ethoxylates, alkyl-PEG dimethicones, lauryl PEG-8 dimethicone (trade name SILUBE® J208-612), lauryl PEG-8 dimethicone (trade name SILUBE® J208-812), and combinations thereof.

In another embodiment, the polymer with ester linkages comprises, such as but without limitation, i.e., polyglyceryl stearate/isostearate dilinoleate crosspolymer (semi-solid) (trade name COSMOSURF® PG-1S), polyglyceryl stearate/isostearate dilinoleate crosspolymer (liquid) (trade name COSMOSURF® PG2-1S), polyglyceryl stearate/isostearate dilinoleate crosspolymer (solid) (trade name COSMOSURF® PG1-1B), polymers with hydroxyl groups, acidic polymers, saturated acidic polymers with alcohol groups, unsaturated acidic polymers with alcohol groups, stearic acid derivatives, palmitic acid derivatives, behenoate derivatives, and combinations thereof.

In another embodiment, the phenyl silicone, such as but without limitation, i.e., phenylisopropyl dimethicone (trade name SILWAX® DO-MS), polymers with ethylene groups, polymers with phenyl rings, and combinations thereof.

In one embodiment, the synergistic combination of polymers is present in an amount of 0.1 wt. % to about 15 wt. %. In another embodiment, the alkyl dimethicone is present in an amount of about 0.1% to about 5%, and preferably in a range of about 0.1 wt. % to about 1.5 wt. %. In another embodiment, the polymer with ester linkages is present in an amount of about 0.1 wt. % to about 5 wt. %, and preferably in an amount of about 0.1 wt. % to about 1.5 wt. %. In another embodiment, the phenyl silicone is present in an amount of about 0.1 wt. % to about 5 wt. %, and preferably in a range of about 0.1 wt. % to about 1.5 wt. %.

In another embodiment, the photoprotective composition further comprises an abietic acid and ester derivatives. The abietic acid and ester derivatives thereof can comprise, but is not limited to, i.e., hydrogenated methyl abietate (trade name MERISTANT® L), hydrogenated glyceryl abietate (trade name MERISTANT® S). In one embodiment, the abietic acid and ester derivatives is present in an amount of less than or equal to about 5 wt. %, based on the total weight of the composition. In another embodiment, the abietic acid and ester derivatives is present in an amount of between about 0.1 wt. % and about 1.5 wt. %.

In another embodiment, the photoactive composition may additionally comprise at least one aliphatic hydrocarbon, such as but without limitation, i.e., isohexadecane (trade name PERMETHYL® 101A), isododecane (trade name PERMETHYL® 99A), mineral oil such as those known by trade name Drakeol Light Mineral Oil, waxes such as Lotus Wax, $C_{13}$ to $C_{22}$ alkenes, $C_{12}$ to $C_{16}$ isoparaffins such as those known by trade names LILAC® and SiClone® SR-5, hydrogenated polyisobutene such as those know by trade names PANALANE® L14E, hydrogenated polyisobutene such as those known by trade names PANALANE® H300E, methylpropanediol sold under the trade name MP DIOL, and combinations thereof.

In one embodiment, the at least one aliphatic hydrocarbon is present in an amount less than or equal to about 75 wt. %, based on the total weight of the photoprotective composition. In another embodiment, the at least one aliphatic hydrocarbon is present in an amount of about 10 wt. % to about 75 wt. %, based on the total weight of the photoprotective composition. In yet another embodiment, the at least one aliphatic hydrocarbon is present in an amount between about 10 wt. % and about 50 wt. %, based on the total weight of the photoprotective composition. In one embodiment, the aliphatic hydrocarbon comprises isohexadecane and isododecane.

In another embodiment, the photoactive composition may additionally comprise at least one ester, such as but without limitation, i.e., octyldodecyl citrate cross polymer (trade name COSMOSURF® CE-100), cetearyl ethylhexanoate (trade name SCHERCEMOL 1688), ethylhexyl palmitate (trade name CERAPHYL® 368), isononyl isononanoate (trade name DERMOL 99), octyldodecyl neopentanoate (trade name ELEFAC® 1-205), isodecyl neopentanoate (trade name BERNEL Ester 105), decyloleate (trade name CERAPHYL® 140), capric triglycerides and caprylic triglycerides such as those known by trade name DERMOL M5, isopropyl myristate (trade name DERMOL IPM), diisopropyl adipate (trade name CERAPHYL® 230), dibutyl adipate (trade name CETIOL® B), ethylhexyl benzoate (trade name FINSOLV® EB), $C_{12}$ to $C_{15}$ alkyl benzoate (trade name FINSOLV® TN), neopentyl glycol diethylhexanoate (trade name SCHERCEMOL NGDO Ester), dioctyl malate (trade name CERAPHYL® 45), glyceryl dilaurate (trade name EMULSYNT GDL) and combinations thereof.

In one embodiment, the at least one ester is present in an amount less than or equal to about 75 wt. %, based on the total weight of the photoprotective composition. In another embodiment, the at least one ester is present in an amount of about 20 wt. % to about 60 wt. %, based on the total weight of the photoprotective composition.

The photoprotective composition with the synergistic combination of polymers provides for a substantially complete film, an improved film formation, increased uniformity in film formation, increased film durability, increased total UVA and/or UVB absorbance, increased UVR absorbance, increased broad spectrum coverage, increased breadth of broad spectrum coverage, increased magnitude in broad spectrum coverage, water resistance, and combinations thereof.

Film formation can be characterized by a plurality of factors, such as, i.e., how the film performs or withstands water (i.e., water-resistantance), how the film performs or withstands sweat (i.e., sweat-resistantance), how the film performs or withstands rubbing, lathering, oscillating and or any contact that could potentially abrade the film (i.e., rub-resistantance), and/or how the film performs under increased heat (i.e., heat-resistantance). Further film properties that can assist in characterizing films and how effective those films are is how adhesive and/or cohesive the film is. Adhesion can be described as, for example, how likely the film is going to stick or adhere to a substrate. In other words, a film that is adhesive is likely to, upon application to a substrate, remain on a substrate for a reasonable period of time. A film may further be adhesive such that it remains on a substrate for a significant period of time through any or all of the plurality of factors noted above.

Cohesion can be described as, for example, the amount or level of attraction between molecules within the film. The amount or level of attraction between molecules can be attributed by, but not limited to, types of bonds, the number bonds, the bonding energies, and combinations thereof. For instance, a cohesive film is one wherein the film is able to maintain a substantially continuous film with a consistent dispersion upon a substrate. In other words, the film is not, in one extreme, i.e., running, or pooling, or alternatively, in another extreme, is not completely rigid or unbending.

Balancing adhesion and cohesion is critical in creating a substantially complete film (i.e. a uniform and/or durable film). For instance, a film that does not adhere to a substrate for a reasonable period of time will not provide the photoprotective composition the ability to provide photoprotection to the substrate it was supposed to adhere to. In another instance, if the film adheres to rigidly to a substrate, the photoprotective composition may not be uniform, i.e., be able to flex with substrate, should the substrate move, be moved, or if the substrate is touched by another object, and as such, the film may be disturbed such that at least a portion of the entire substrate that initially had a film adhered to it is no longer photoprotected. In another instance, if the cohesion of the film is too little, the film may never be able to evenly adhere to the substrate and thus the entire substrate may not be uniformly photoprotected, or protected at all. By the same token, if the film is overly cohesive, the film may not be dispersible onto the substrate, and thus no even or uniform application, distribution, dispersal and/or adhesion to the substrate would leave at least a portion of the substrate vulnerable (i.e. without photoprotection). One skilled in the art recognizes balancing adhesion and cohesion is clearly a challenge upon initial removal of the photoprotective composition from a container, upon application of a photoprotective composition to a substrate, upon rubbing, lathering and oscillating the photoprotective composition onto, into and/or over a substrate, and also upon allowing the photoprotective composition an opportunity to dry after application to the substrate such that time has passed and the film can endure water, sweat, rubbing, heat, and combinations thereof.

Figure 2:
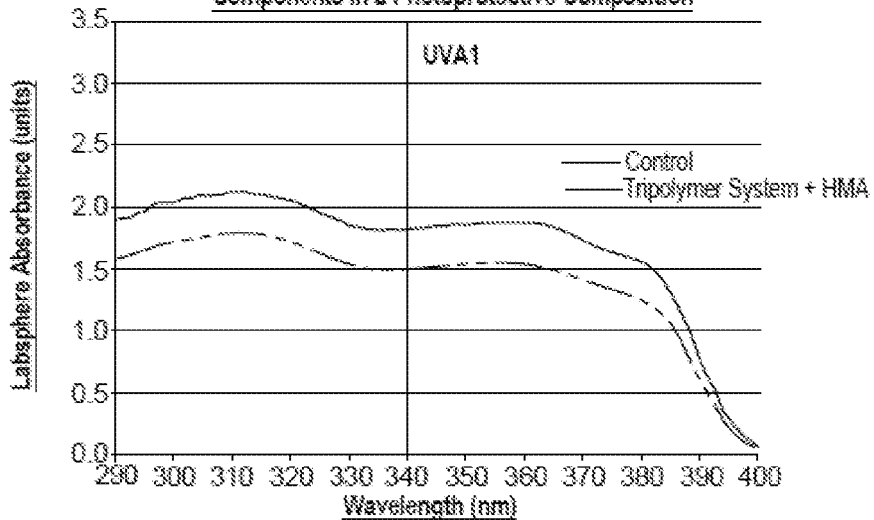
FIG. 2 is a chart showing UVR absorption of photoprotective compositions

As herein described, it has been unexpectedly found that when certain components that do not innately absorb UVR are combined, a total magnitude of UVR absorbance or the breadth of UVR absorbance coverage, or both, are unexpectedly increased. FIG. 1 represents an embodiment of this unexpected magnitude increase in UVR absorbance; FIG. 2 represents an embodiment of this unexpected magnitude and breadth increase in UVR absorbance. Table 1 provides such UVR information for such components neat (i.e., solely, without any other additives).

TABLE 1

| | UVR Absorption Neat Materials | |
|---|---|---|
| Component | UVB @ 310 nm | UVA1 @ 370 nm |
| Hydrogenated Methyl Abietate | 0 unit | 0 unit |
| Hydrogenated Glyceryl Abietate | 0 unit | 0 unit |
| Lauryl PEG-8 Dimethicone | 0 unit | 0 unit |
| Phenylisopropyl Dimethicone | 0 unit | 0 unit |
| Polyglyceryl-3 Stearate/Isostearate Dilinoleate Crosspolymer | 0 unit | 0 unit |

As shown above, none of the exemplary components innately provide UVR absorbance. As shown in FIG. 1, when an exemplary combination of the above noted components are added to a base photoprotective composition, a significant magnitude increase in SPF is realized.

The determination of in-vitro static SPF was accomplished with Labsphere UV-2000S Transmittance Analyzer, Schonberg Sun PMMA HD2 plates, and the product application was scaled down to 1 mg/cm$^2$ for the signal to remain within the acceptable range of the instrument. Critical wavelength was accomplished in-house according to the guidelines set forth in the 2011 Sunscreen final rule, which is codified in the FDA regulations 21 C.F.R. 201.327. Instrumentation included the Labsphere UV 2000-S Transmittance Analyzer, Solar Simulator with 300 W xenon arc lamp and a PMA 2100 radiometer with a UVB PMA 2101 Sensor. The substrate utilized was the Schonberg Sun PMMA HD2 plates. For the in-vitro FDA critical wavelength (CW) determination, the specified product application dose of 0.75 mg/cm' was used.

TABLE 2

UV Absorption Synergy of Polymer Compositions + HMA in Photoprotective* Compositions

| Sample ID | Ingredients (wt. %) | Ratio | in-vitro SPF (units) | |
|---|---|---|---|---|
| C1 | Control | — | 45 ± 2 STD | |
| C3 | DOMS | 1.0 | 51 ± 1 STD | +6 |
| C4 | PG1 | 1.0 | 60 ± 2 STD | +15 |
| C5 | 612 | 1.0 | 52 ± 2 STD | +7 |
| B6 | DOMS/PG1/612 | 0.5/1.0/1.0/1.0 | 73 | Theoretical |
|  | DOMS/PG1/612 | 0.5/1.0/1.0/1.0 | 80 ± 2 STD | Observed |
| A1 | Control | — | 45 ± 2 STD | |
| A2 | HMA | 0.5 | 51 ± 1 STD | +6 |
| A3 | DOMS | 1.0 | 51 ± 1 STD | +6 |
| A4 | PG1 | 1.0 | 60 ± 2 STD | +15 |
| A5 | 612 | 1.0 | 52 ± 2 STD | +7 |
| A6 | HMA/DOMS/PG1/612 | 0.5/1.0/1.0/1.0 | 79 | Theoretical |
| A6 | HMA/DOMS/PG1/612 | 0.5/1.0/1.0/1.0 | 88 ± 2 STD | Observed |

*10 wt. % homosalate, 5 wt. % octisalate, 5 wt. % octocrylene, 3 wt. % avobenzone
HMA = MERISTANT ® L
DOMS = SILWAX ® DO-MS
PG1 = COSMOSURF PG1-IS
612 = SILUBE ® J 208-612
Dose: 1.0 mg/cm$^2$, Schonberg HD2 PMMA Substrate As shown above, the exemplary embodiments wherein one component is added to the control (i.e. base) composition generally improve the in-vitro SPF scores of the photoprotective composition. It is further shown that the observed (i.e., actual) in vitro-SPF values obtained were higher than theoretical values. Furthermore, tested embodiment A6 including HMA provided the highest theoretical and observed in-vitro SPF values. More particularly, the exemplary test embodiment A6 unexpectedly and incredibly provided a 10.2% increase in the observed SPF over the theoretical SPF value.

Figure 3A:
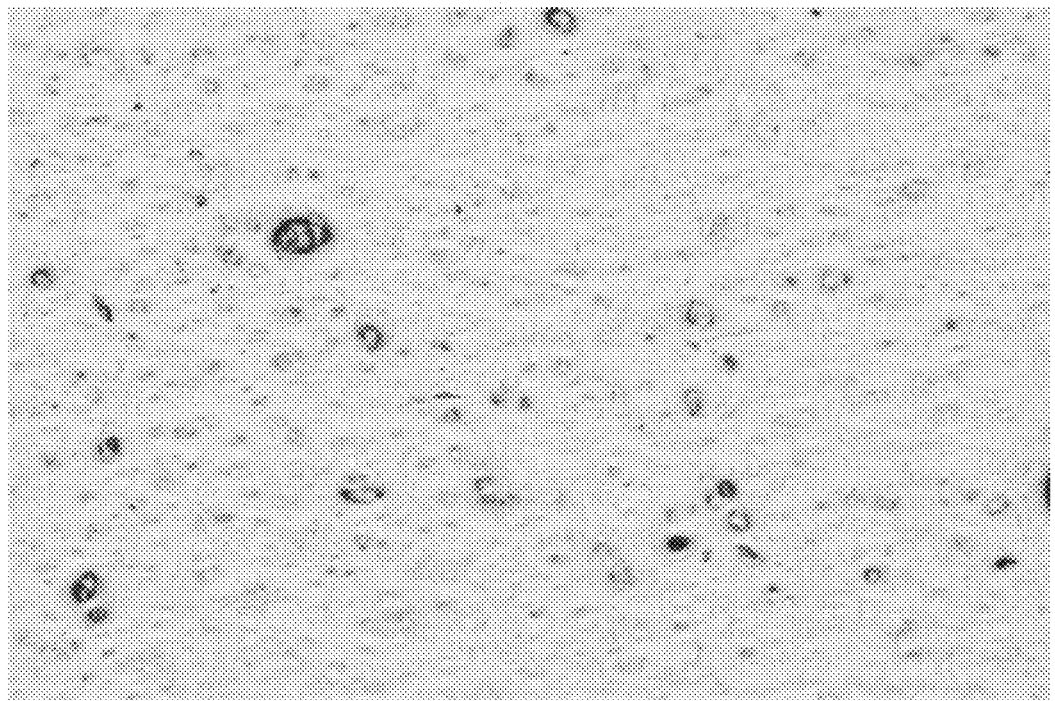
FIG. 3A is an image of film formation of a photoprotective composition
Figure 3B:
FIG. 3B is an image of film formation of a photoprotective composition
Figure 3C:
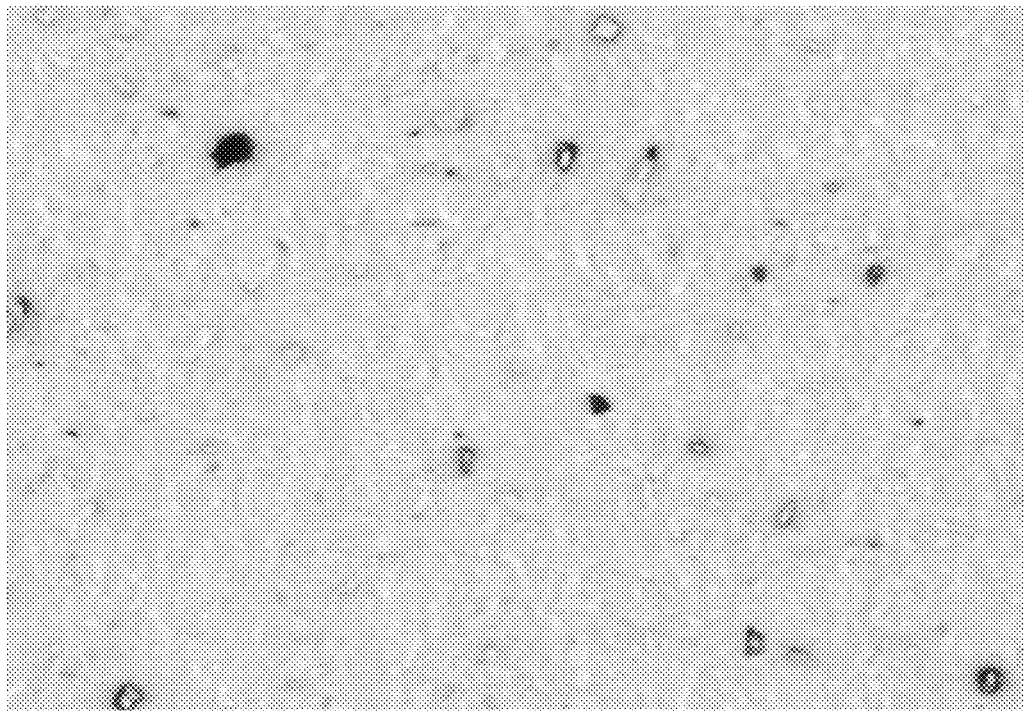
FIG. 3C is an image of film formation of a photoprotective composition
Figure 3D:
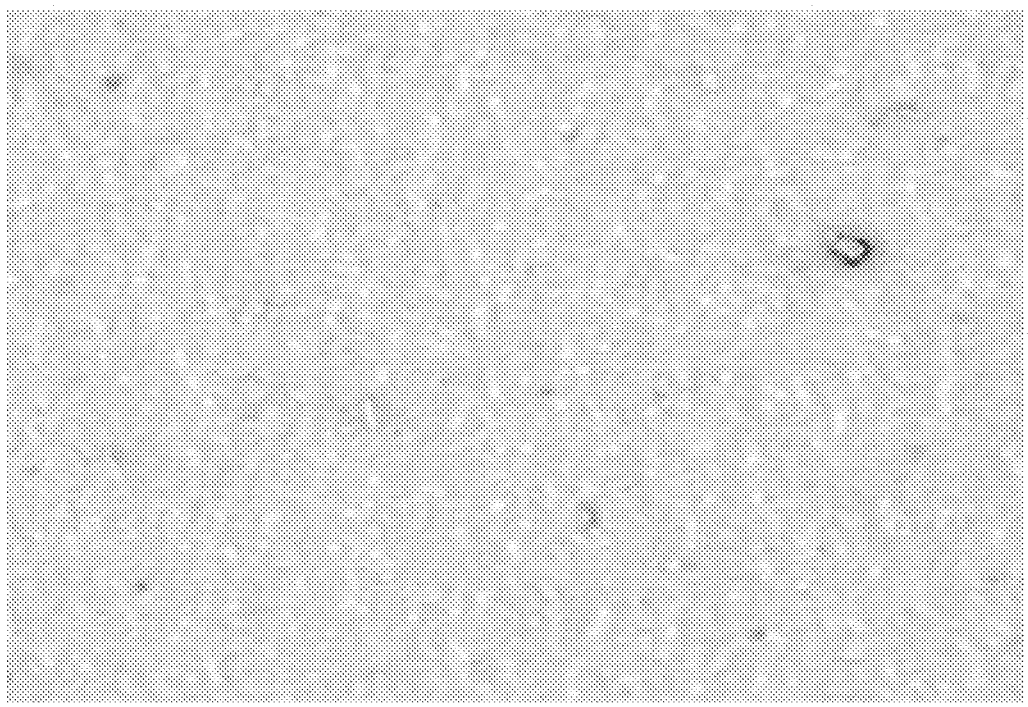
FIG. 3D is an image of film formation of a photoprotective composition

As shown in FIGS. 3A-3D, each of the exemplary components tested with the control (i.e., base) composition provided different films. For instance, the photoprotective composition with HMA provided the least uniform coverage, as many of the rough PMMA substrate projections remained uncovered. In the alternative, the photoprotective composition comprising PG1 provided the most complete and/or uniform coverage. FIG. 3A shows an embodiment comprising HMA, such as, i.e., exemplary test embodiment A2. FIG. 3B shows an embodiment comprising DOMS, such as, i.e., exemplary test embodiment A3 and/or C3. FIG. 3C shows an embodiment comprising 612, such as, i.e., exemplary test embodiment A5 or C5. FIG. 3D shows an embodiment comprising PG1, such as, i.e., exemplary test embodiment A4 or C4.

As shown below in Table 3, combining HMA and DOMS in certain percentages with the control (i.e. base) composition unexpectedly yielded lower performing photoprotective compositions. Tested embodiment B1, as shown not only had a decrease in vitro SPF and UVA1 absorbance, it also was visually less-appealing in that it was hazy.

TABLE 3

UVR Absorption Responses of Polymer Composition and/or HMA Components in Photoprotective* Compositions

| | | | | | | Absorption Response | |
|---|---|---|---|---|---|---|---|
| Sample | Ingredient Ratio | | | | in-vitro SPF | UVA1 | |
| ID | HMA | DOMS | PG1 | 612 | (units) | ($\lambda$ nm @0.5 abs) | |
| C1 | — | — | — | — | 45 ± 2 STD | 391.0 | |
| C2 | 0.5 | — | — | — | 51 ± 1 STD | 391.5 | |
| C3 | — | 1.0 | — | — | 51 ± 1 STD | 391.5 | |
| C4 | — | — | 1.0 | — | 60 ± 2 STD | 392.0 | |
| C5 | — | — | — | 1.0 | 52 ± 2 STD | 391.5 | |
| C6 | 0.5 | 1.0 | 1.0 | 1.0 | 88 ± 2 STD | 392.5 | |
| B1 | 0.5 | 1.0 | — | — | 35 ± 2 STD Hazy | 390.5 | |
| B2 | 0.5 | — | 1.0 | — | 56 ± 2 STD | 391.5 | |
| B3 | 0.5 | — | — | 1.0 | 62 ± 1 STD | 391.5 | |
| B4 | — | — | 1.0 | 1.0 | 67 ± 3 STD | 393.0 | |
| B5 | — | 1.0 | 1.0 | — | 69 ± 1 STD | 391.5 | |
| B6 | — | 1.0 | 1.0 | 1.0 | 80 ± 2 STD | 392.0 | |

*10 wt. % homosalate, 5 wt. % octisalate, 5 wt. % octocrylene, 3 wt. % avobenzone
HMA = MERISTANT ® L
DOMS = SILWAX ® DO-MS
PG1 = COSMOSURF PG1-IS
612 = SILUBE ® J 208-612
Dose for in vitro SPF Method: 1 mg/cm$^2$, Schonberg HD2 PMMA Plates
Dose for FDA CW Method: 0.75 mg/cm$^2$, Schonberg HD2 PMMA Plates As shown, above in Table 3, embodiments C6 and B6 comprising at least polymers DOMS, PG1 and 612 were shown to provide significantly improved SPF and/or significantly improved UVA1 absorbance. In other words, polymers DOMS, PG1 and 612 were an unexpectedly synergistic polymer composition that provided a significant increase in the magnitude and/or breadth of UVR absorbance, as exemplified by the in vitro SPF and UVA1 test results in Table 3. As shown more particularly in embodiment C6 comprising DOMS, PG1, 612 and HMA, a further synergy exists between the synergistic polymers and HMA; the DOMS, PG1, 612 and HMA provided an even further significant increase in the magnitude and/or breadth of UVR absorbance, as exemplified by the in vitro SPF and UVA1 test results in Table 3, The example prototype compositions shown above in Table 1 as demonstrated in at least Table 3, minimally meet a critical wavelength of 370 nm to qualify for the broad spectrum protection claim when combined with the control (i.e., base) photoprotective composition C1, As demonstrated by the embodiments of the photoprotective composition of the present disclosure, the photoprotective composition can provide a critical wavelength of greater than or equal to 390.0 nm. In some embodiments, the photoprotective composition of the present disclosure can provide a critical wavelength of greater than or equal to 391.0 nm. In further embodiments, the photoprotective composition of the present disclosure can provide a critical wavelength of greater than or equal to 392.0 nm. In yet further embodiments, the photoprotective composition of the present disclosure can provide a critical wavelength of greater than or equal to 392.5 nm.

Table 4 shows similar unexpected results upon combing components such as, i.e., HMA and DOMS to the control (i.e. base) composition.

TABLE 4

Effect of HMA on UV Absorption Energy of Polymer Composition Components in Photoprotective* Compositions

| Sample ID | Ingredients | Ratio | in-vitro SPF (units) | |
|---|---|---|---|---|
| A1 | Control | — | 45 ± 2 STD | |
| A3 | HMA | 0.5 | 51 ± 1 STD | +6 |
| B1 | HMA/DOMS | 0.5/1.0 | 35 ± 2 STD | −10 Hazy |
| B4 | HMA/PG1 | 0.5/1.0 | 56 ± 2 STD | +11 |
| B5 | HMA/612 | 0.5/1.0 | 62 ± 2 STD | +17 |
| A5 | 612 | 1.0 | 52 ± 2 STD | +6 |
| B5 | HMA/612 | 0.5/1.0 | 58 | Theoretical |
| B5 | HMA/612 | 0.5/1.0 | 62 ± 2 STD | Observed |

Figure 4A:
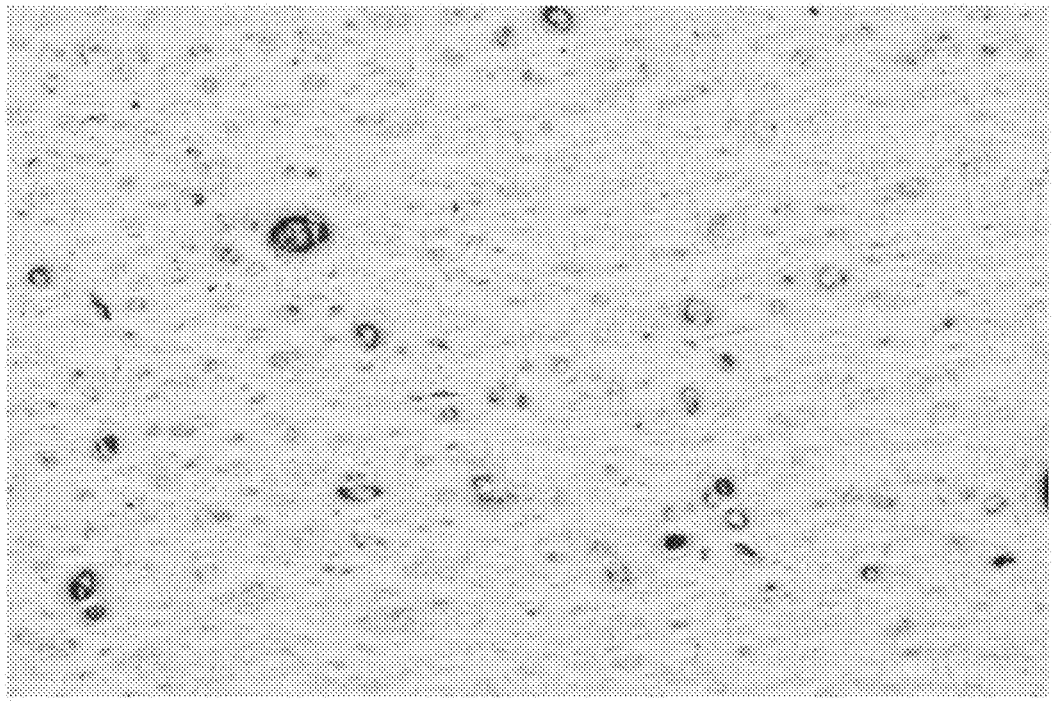
FIG. 4A is an image of film formation of a photoprotective composition
Figure 4B:
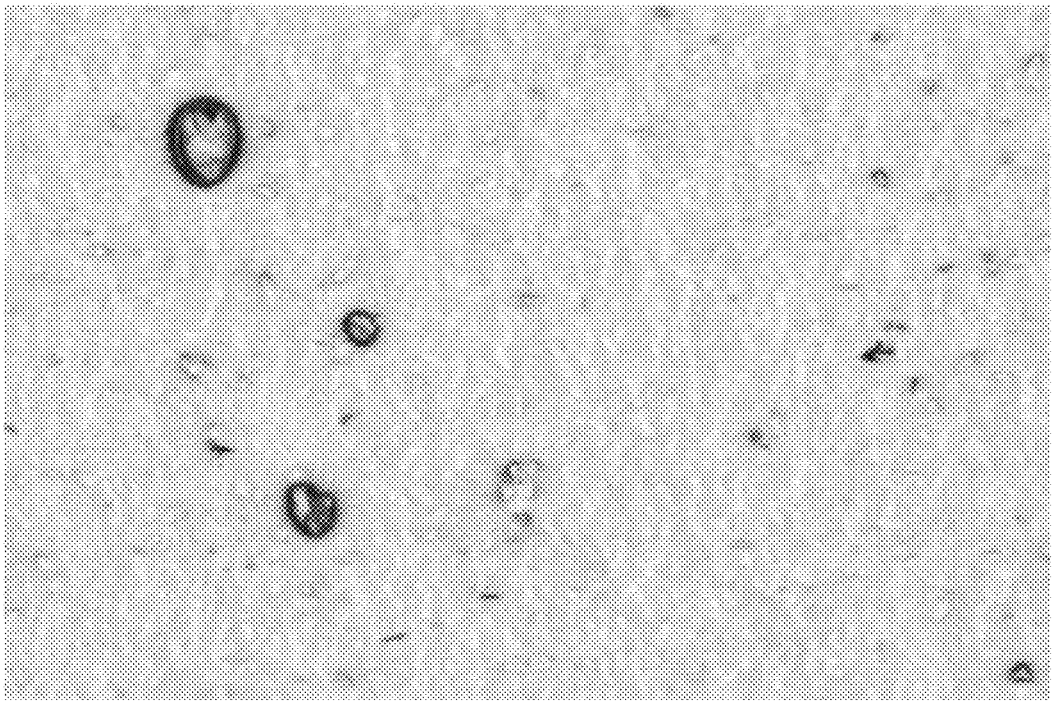
FIG. 4B is an image of film formation of a photoprotective composition
Figure 4C:
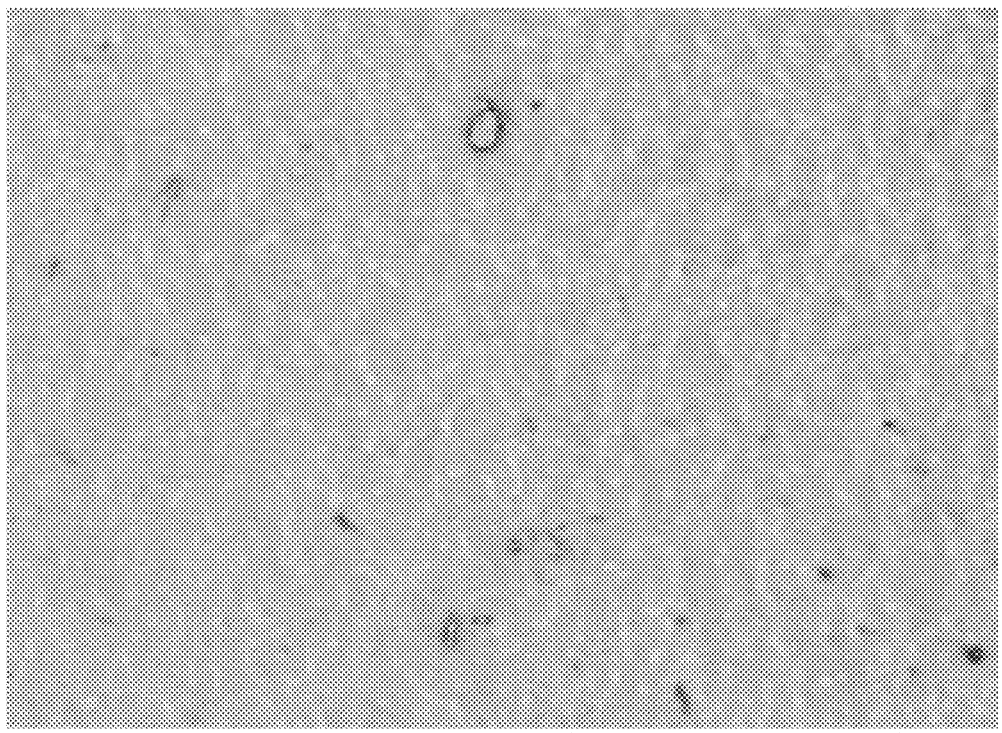
FIG. 4C is an image of film formation of a photoprotective composition
Figure 4D:
FIG. 4D is an image of film formation of a photoprotective composition

*10 wt. % homosalate, 5 wt. % octisalate, 5 wt. % octocrylene, 3 wt. % avobenzone
HMA = MERISTANT ® L
DOMS = SILWAX ® DO-MS
PG1 = COSMOSURF PG1-IS
612 = SILUBE ® J 208-612
Dose: 1.0 mg/cm$^2$, Schonberg HD2 PMMA Substrate These results are further compared with FIGS. 4A-4D. For instance, the photoprotective composition with both HMA and 612 as shown in FIG. 4C provided the most uniform film, while the photoprotective compositions having HMA and PG1 as shown in FIG. 4D or HMA and DOMS as shown in FIG. 4B did not provide such uniformity. As shown in FIG. 4A, a composition with HMA such as, i.e., test embodiment A3, provided the least uniformity.

The determination of in-vivo SPF very water resistance (VWR) was accomplished at Harrison Research, Laboratories, Union, N.J., according to the guidance provided in 21 CFR 201327 specifying a product application dose of 2 mg/cm2 on human subjects. Additionally, according to the 2011 FDA Rule for Very Water Resistance test method, the tested embodiments of photoprotective compositions of the present disclosure meet the minimum 370 nm critical wavelength criteria, thus establishing the broad spectrum photoprotective nature of the present disclosure's photoprotective compositions.

Further surprisingly and unexpectedly, the tested embodiments of photoprotective compositions shown in Tables 5-8 (i.e., tested embodiments D1 through D7) performed well in the water resistance efficacy testing. The results as demonstrated in Tables 5-8 below indicate that the tested embodiments of the photoprotective compositions of the present disclosure performed well on for a product with an SPF rating of 50+.

Tables 5-8 further show that high alcohol, low alcohol and/or no alcohol photoprotective compositions are all within the scope of the present disclosure. Tables 5-8 show that photoprotective compositions with high alcohol, low alcohol and no alcohol all provide photoprotection that meets, such as but not limited to, i.e., the 2011 FDA Rule for Very Water Resistance test method, the 2012 ISO 24443 test method, the Australia/New Zealand 2604:2012 test method, and combinations thereof, and maintains a UVR absorbance value such as, but not limited to, an SPF of 50+, a 1/3 UVAPF/SPF ratio, an FDA critical wavelength of at least 370 nm, and combinations thereof.

TABLE 5 in vivo FDA SPF Very Water Resistance Efficacy for Polymer Compositions + HMA in Photoprotective* High Alcohol Compositions

| Study # | Components | Ratio | in-vivo SPF VWR Subject Scores | in-vivo SPF VWR Average |
|---|---|---|---|---|
| D1 | HMA/DOMS/ PG1/612 | 0.5/1.0/1.0/1.0 | 65.00, 65.00, 65.00 | 65.00 |
| D2 | HMA/DOMS/ PG1/612 + Additional Film Former** | 0.25/0.5/0.5/0.5 | 52.17, 60.00, 60.00 | 57.39 |
| | | | Difference | +7.61 |
| | | | | 11.7% increase |

*Homosalate 10 wt. %, Octisalate 5 wt. %, Octocrylene 5 wt. %, Avobenzone 3 wt. %
**20 wt. % Isododecane
HMA = MERISTANT ® L
DOMS = SILWAX ® DO-MS
PG1 = COSMOSURF PG1-IS
612 = SILUBE ® J 208-612
Dose for in vivo SPF VWR: 2 mg/cm$^2$, human subjects As shown in Table 5 above, exemplary tested embodiments D1 and D2 both provide an average in vivo SPF VWR of 50+. While formula D1 shows that doubling the concentrations of HMA, DOMS, PG1 and 612 increase the in vivo SPF VWR, both are sufficient for achieving a 50+ product. Furthermore, exemplary tested embodiments D1 and D2 show that the synergy amongst at least the synergistic polymer composition is unexpected. D2 shows that by decreasing the concentrations of the synergistic polymer composition and HMA and adding a further film forming agent does not yield the same UVR absorbance properties of D1. Nonetheless, D2 sufficiently provides UVR absorbance of well over an SPF 50+. Furthermore, the exemplary embodiment D1 achieved a 7.61% increase in SPF as per the FDA SPF VWR test. As such, exemplary tested embodiments show that the present disclosure's photoprotective compositions can advantageously increase the magnitude and breadth of UVR absorbance to a level that accommodates any or all global regulatory absorbency caps, with very small quantities of synergistic polymer compositions.

TABLE 6 in vivo FDA SPF Very Water Resistance Efficacy
for Polymer Compositions + HMA in Photoprotective*
Low Alcohol Compositions

| Study # | Components | Ratio | in-vivo SPFVWR Subject Scores | in-vivo SPFVWR Average |
|---|---|---|---|---|
| D3 | HMA/DOMS/ PG1/612 + Additional Film Former** | 0.5/1.0/1.0/1.0 | 65.00, 65.00, 65.00 | 65.00 |
| D4 | HMA/DOMS/ PG1/612 + Additional Film Former** | 0.25/0.5/0.5/0.5 | 69.00, 52.17, 60.00 | 60.39 |
| | | | Difference | +4.61 7.2% increase |

*Homosalate 10 wt. %, Octisalate 5 wt. %, Octocrylene 5 wt. %, Avobenzone 3 wt. %
**20 wt. % Isododecane
HMA = MERISTANT ® L
DOMS = SILWAX ® DO-MS
PG1 = COSMOSURF PG1-IS
612 = SILUBE ® J 208-612
Dose for in vivo SPF VWR: 2 mg/cm², human subjects Table 6 shows that additional film formers can be added to further improve the performance of the synergistic polymer composition, the synergistic polymer composition and HMA, and combinations thereof. Comparing the additional film former additions of Table 5 (20 wt. % isohexadecane) and Table 6 (20 wt. % isododecane), one skilled in the art understands that adding additional different film formers in varying concentrations to any or all of HMA, DOMS, PG1 and 612 is within the scope of the present disclosure and yet further reaffirms how unexpected the synergistic combination of the DOMS, PG1 and 612 composition is, and furthermore, that DOMS, PG1 and 612 composition with HMA. More specifically, a 7.2% increase was achieved by exemplary test embodiment D4 in comparison to exemplary test embodiment D3, which identifies the unexpected synergies amongst polymers that have been discovered and described within the present disclosure.

TABLE 7

| Study # | Components | Ratio | Test | in-vivo SPFVWR Average |
|---|---|---|---|---|
| in vivo SPF Increased Duration Water Resistance Efficacy for Polymer Compositions + HMA in Photoprotective* High Alcohol Compositions | | | | |
| D1 | HMA/DOMS/ PG1/612 | 0.5/1.0/1.0/1.0 | FDA SPFVWR 4 hr. | 68.67 n = 3 |
| D5 | HMA/DOMS/ PG1/612 | 0.5/1.0/1.0/1.0 | AU/NZ SPFWR 4 hr. | Static: 65.00; n = 3 WR: 53.90; n = 3 |
| in vitro UVA Determination Polymer Compositions + HMA in Photoprotective* High Alcohol Compositions | | | | |
| D5 | HMA/DOMS/ PG1/612 | 0.5/1.0/1.0/1.0 | FDA CW ≥370 nm | 376 nm |
| D5 | HMA/DOMS/ PG1/612 | 0.5/1.0/1.0/1.0 | ISO 24443 | UVAPF = 26.1 UVAPF/SPF = 0.44 |

*Homosalate 10 wt. %, Octisalate 5 wt. %, Octocrylene 5 wt. %, Avobenzone 3 wt. %
HMA = MERISTANT ® L
DOMS = SILWAX ® DO-MS
PG1 = COSMOSURF PG1-IS
612 = SILUBE ® J 208-612
Dose for in vitro SPF Method: 1 mg/cm², Schonberg HD2 PMMA Plates
Dose for in vivo SPF VWR: 2 mg/cm², human subjects
Dose for FDA CW Method: 0.75 mg/cm², Schonberg HD2 PMMA Plates As shown in Table 7 above, exemplary test embodiments D1 and D5 achieved a score a UVAPF value of 26.1 (0.44 UVAPF/SPF), and also exhibited an ISO 24443 method (post irradiation) critical wavelength of 376 nm. In one embodiment, the photoprotective composition meets the 1/3 UVA ratio requirement of ISO 24443. In some embodiments, an SPF VWR 50+ is achieved over a period of forty (40) minutes, and/or eighty (80) minutes. In further embodiments, a static SPF of 65 and/or a water resistance of 50+ are achieved as per the Australia/New Zealand Water Resistance test method.

Table 8 further shows the increased UVR absorbance of tested embodiments of the present disclosure under other test methodologies, namely the "wet skin" FDA Very Water Resistant test method and the Australia/New Zealand test method. In the "wet skin" FDA Very Water Resistant study, ten (10) human subjects were pre-immersed for five (5) minutes to hydrate the skin, and then the photoprotective composition was applied immediately to wet skin so that air drying could not occur between immersion and application steps. The human subjects were then treated according to the FDA SPFVWR assay. Exemplary test embodiments D1 and D5 maintained an SPF rating of 50+.

TABLE 8 in vivo FDA SPFVWR Efficacy Modified for Wet Skin Pretreatment
Polymer Compositions + HMA in Photoprotective* Compositions

| Study # | Components | Ratio | in-vivo SPFVWR Subject Scores | in-vivo SPFVWR @95% CI |
|---|---|---|---|---|
| D5 | HMA/DOMS/ PG1/612 | 0.5/1.0/1.0/1.0 | High Alcohol Wet Skin SPFVWR | 56.89 n = 10 |
| D6 | HMA/DOMS/ PG1/612 + Additional Film Former** | 0.5/1.0/1.0/1.0 | Low Alcohol Wet Skin SPFVWR | 55.34 n = 10 |
| D7 | HMA/DOMS/ PG1/612 + Additional Film Former*** | 0.12/0.25/1.0/ 0.25 | No Alcohol Wet Skin SPFVWR | 58.21 n = 10 |

*Homosalate 10 wt. %, Octisalate 5 wt. %, Octocrylene 5 wt. %, Avobenzone 3 wt. %
**20 wt. % Isododecane
***20 wt. % Isohexadecane
HMA = MERISTANT ® L
DOMS = SILWAX ® DO-MS
PG1 = COSMOSURF PG1-IS
612 = SILUBE ® J 208-612
Dose for in vivo SPF VWR: 2 mg/cm², human subjects
Dose for FDA CW Method: 0.75 mg/cm², Schonberg HD2 PMMA Plates As demonstrated in the exemplary test embodiments in Tables 5-8 above, the exemplary test embodiments have efficacy on both dry and wet substrates.

Both in vitro and in vivo results indicated that SPF can be boosted with polymer compositions. Furthermore, including additional film formers such as but not limited to, i.e., isohexadecane or isododecane, or both, were able to maintain or further boost SPF, depending on the amount of alcohol in the formula. Results further indicate that SPF can be further boosted by adding HMA and polymer compositions.

As shown above, some embodiments of the photoprotective composition are water-resistant. In one embodiment, the photoprotective composition meets the Sun Protection Factor Very Water Resistance threshold. In another embodiment, the photoprotective composition may be suitable for sustaining water-resistance for at least forty (40) minutes. In a further embodiment, the photoprotective composition may be suitable for sustaining water-resistance for at least eighty (80) minutes. In other embodiments the photoprotective composition may be suitable to sustain a suitable level of photoprotection, as demonstrated by any or all of the FDA critical wavelength method for a period of forty (40), and/or eighty (80) minutes. In further embodiments, the photoprotective composition is capable of sustaining an FDA SPF rating of 15, 30, 50, or 50+, for a period of forty (40) and/or eighty (80) minutes, as exemplified under the FDA VWR test method. Furthermore, some embodiments of the photoprotective compositions of the present disclosure achieved a water resistance passing score for four (4) hours under the Australia/New Zealand standard. As such, some embodiments, whether the embodiments are high alcohol, low alcohol, or no alcohol embodiments, are able to pass a SPF very water resistance threshold such that SPF protection of 15, 30, 50, and/or 50+ is provided after forty (40), eighty (80) minutes, and/or four (4) hours under a variety of global standards provided by a plurality of global regulatory bodies. It is quite unexpected and remarkable that a formula is capable of achieving one of the above-mentioned standards, let alone all of them, as has been accomplished by embodiments of the present disclosure.

As exemplified throughout the present disclosure, one skilled in the art the synergistic polymer composition of the present disclosure is advantageous for several reasons. The synergistic polymer composition can provide a surprising increase in magnitude or breadth of photoprotection (or both), as demonstrated in the various test methods and results related thereto throughout this disclosure. The synergistic polymer composition is also advantageous, as it can permit a manufacturer to reduce the percentages of any or all photoactive agents utilized (as a percentage of the total composition) and still maintain the same magnitude and breadth in photoprotection (or both), as demonstrated in the various test methods and results related thereto throughout the disclosure. In jurisdictions having a photoprotection cap, i.e., in the United States where there is a cap of SPF 50+, it is particularly advantageous to enable the reduction of expensive photoactive agents as a percentage of the total composition and still maintain the same SPF rating.

Figure 5A:
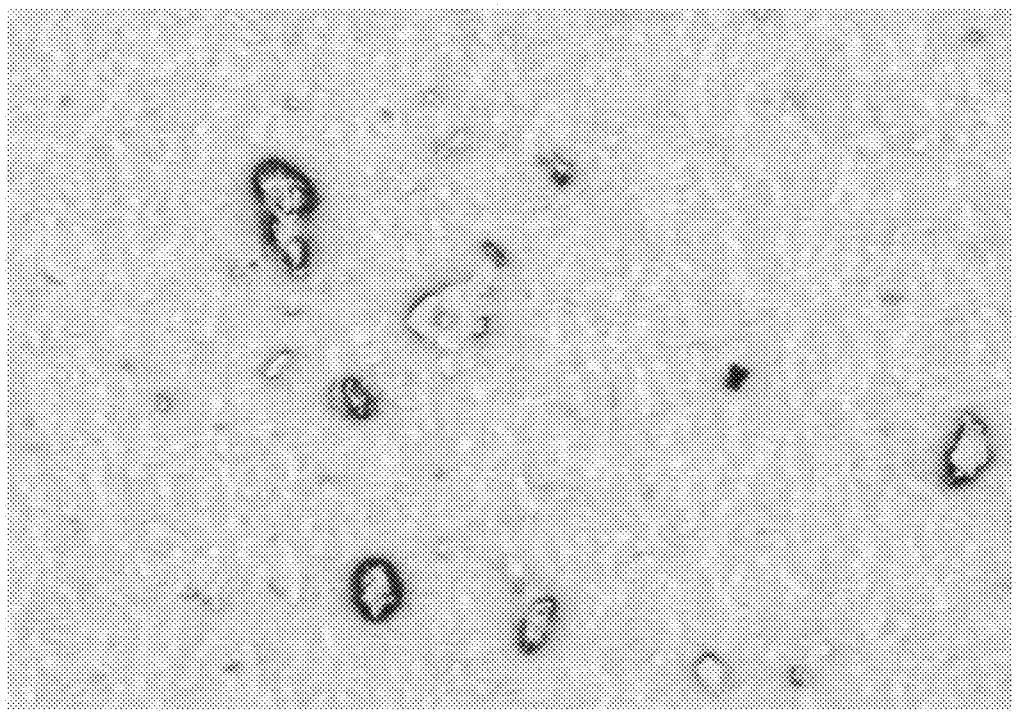
FIG. 5A is an image of film formation of a photoprotective composition
Figure 5B:
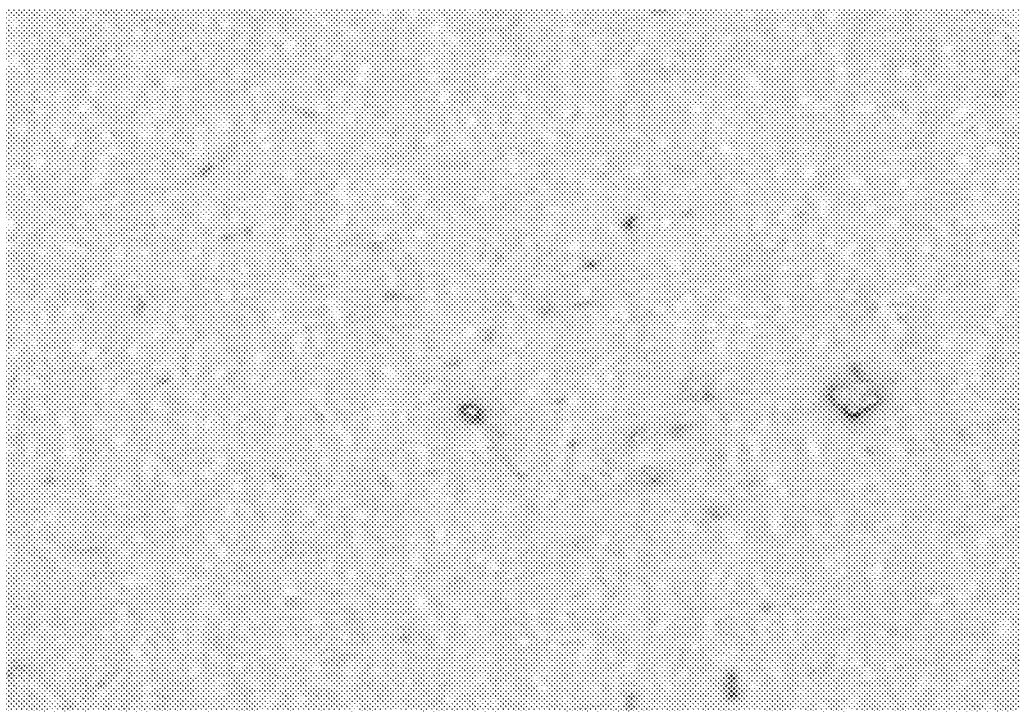
FIG. 5B is an image of film formation of a photoprotective composition

Table 9 below provides a further exemplary embodiment indicating that both a magnitude increase in UVR absorbance and an increased breadth of UVR absorbance are realized when compared to the base photoprotective composition without any components. In the exemplary embodiment, approximately a fifty percent (50%) increase in in vitro SPF is realized, having a standard deviation of plus or minus two. For that matter, the UVA/UVB ratio saw an increase from 0.745 to 0.768, and the breadth of UVR coverage increased from 391.0 nm to 392.5 nm (at 0.5 absorbance). FIG. 2 demonstrates the exemplary embodiment of the photoprotective composition of the present disclosure realized both a magnitude UVR absorbance gain and a gain in breadth of coverage. FIGS. 5A-5B demonstrate the film formation of exemplary test embodiments C1 and C6. Notably, C6 provides a substantially complete film while C1 does not.

TABLE 9

UVR Absorption Responses of Polymer Compositions and HMA Components in Photoprotective* Composition

| Sample ID | Component Ratio | | | | Absorption Response | | |
|---|---|---|---|---|---|---|---|
| | HMA | DOMS | PG1 | 612 | in-vitro SPF (units) | UVA/UVB Ratio | UVA1 (λ nm @0.5 abs) |
| C1 | — | — | — | — | 45 ± 2 STD | 0.745 | 391.0 |
| C6 | 0.5 | 1.0 | 1.0 | 1.0 | 88 ± 2 STD | 0.768 | 392.5 |

*Homosalate 10 wt. %, Octisalate 5 wt. %, Octocrylene 5 wt. %, Avobenzone 3 wt. %
HMA = MERISTANT ® L
DOMS = SILWAX ® DO-MS
PG1 = COSMOSURF PG1-IS
612 = SILUBE ® J 208-612
Dose for in vitro SPF: 1.0 mg/cm$^2$ Schonberg HD2 PMMA Substrate
Dose for FDA CW Method: 0.75 mg/cm$^2$, Schonberg HD2 PMMA Plates As shown in Table 9 above, a striking increase in absorption response (i.e. UVR absorbance, generally) is achieved by including the synergistic polymers DOMS, PG1 and 612 and furthermore including HMA in exemplary test embodiment C6 as compared to C1. Table 10 below further demonstrates the improvement in absorption (i.e. UVR) response at a UVB wavelength of 310 nm and a UVA1 wavelength of 370 nm, as can easily be seen in FIGS. 5A (control) and 5B (polymer composition+HMA).

TABLE 10

Percentage Increase in UVR Response

| | Absorption Units UVB @ 310 nm | Absorption Units UVA1 @ 370 nm |
|---|---|---|
| Control | 1.788 | 1.414 |
| Polymer Composition + HMA | 2.114 | 1.728 |
| Difference (%) | +15.42 | +18.17 |

Dose: 1.0 mg/cm$^2$ Schonberg HD2 PMMA Substrate

Table 10 indicates the exemplary embodiment comprising a polymer composition and HMA provide an incredible increase in both UVB and UVA absorption. Notably, the exemplary embodiment comprising a polymer composition and HMA provides a 15.42% increase in UVB absorption of 2.114 units. Furthermore, the exemplary embodiment also provides an 18.17% increase in UVA absorption of 1.728 units. As such, the present disclosure surprisingly improves both UVB and UVA1 absorbance, amongst other things.

TABLE 11

UVR Absorption Responses of Polymer Compositions + HMA
Components in a Physical Photoprotective Composition

| Sample | Ingredient Ratio | | | | Absorption Response | |
|---|---|---|---|---|---|---|
| ID | HMA | DOMS | PG1 | 612 | in-vitro SPF (units) | UVA1 (λ nm @0.5 abs) |
| B10 | — | — | — | — | 3 ± 0 STD | 364.0 |
| B11 | 0.5 | 1.0 | 1.0 | 1.0 | 10 ± 0 STD | 388.0 |

HMA = MERISTANT ® L
DOMS = SILWAX ® DO-MS
PG1 = COSMOSURF PG1-IS
612 = SILUBE ® J 208-612

Table 11, as shown above, demonstrates the success of polymer compositions and HMA with photoprotective compositions. Table 11 shows the unexpected synergy amongst these polymers and HMA, as demonstrated through the incredible gain in SPF and UVA1 breadth at 0.5 absorbance in physical photoprotection composition.

After establishing an increase of the magnitude or breath of UVR absorbance (or both), further testing established the ability of compositions to form films. The films were compared against existing spray products and an untreated Schonberg HD2 PMMA plate. Table 12 below provides details, as compared to FIGS. 6A-6F.

TABLE 12

| Spray Product | Active Ingredient Content (wt. %) | | | | |
|---|---|---|---|---|---|
| | Homo-salate | Octi-salate | Octo-crylene | Oxy-benzone | Avo-benzone |
| CT Sport 50 | 15.00 | 5.00 | 0.00 | 6.00 | 3.00 |
| CT Wet'n Clear 45+ | 10.00 | 4.50 | 9.00 | 5.00 | 3.00 |
| CT Sport Pro 50+ | 13.00 | 4.50 | 9.00 | 6.00 | 3.00 |
| NT Fresh Cooling 45 | 15.00 | 5.00 | 2.35 | 6.00 | 3.00 |
| NT Wet Skin 50 | 10.00 | 5.00 | 10.00 | 5.00 | 3.00 |
| Aveeno Hydrosport 50 | 10.00 | 5.00 | 10.00 | 5.00 | 3.00 |
| BB Sport 50 | 0.00 | 0.00 | 10.00 | 5.00 | 3.00 |
| Exemplary Embodiment-polymer composition and HMA (SPF 50+) | 10.00 | 5.00 | 5.00 | 0.00 | 3.00 |

Dose: 1.0 mg/cm² Schonberg HD2 PMMA Substrate

Figure 6A:
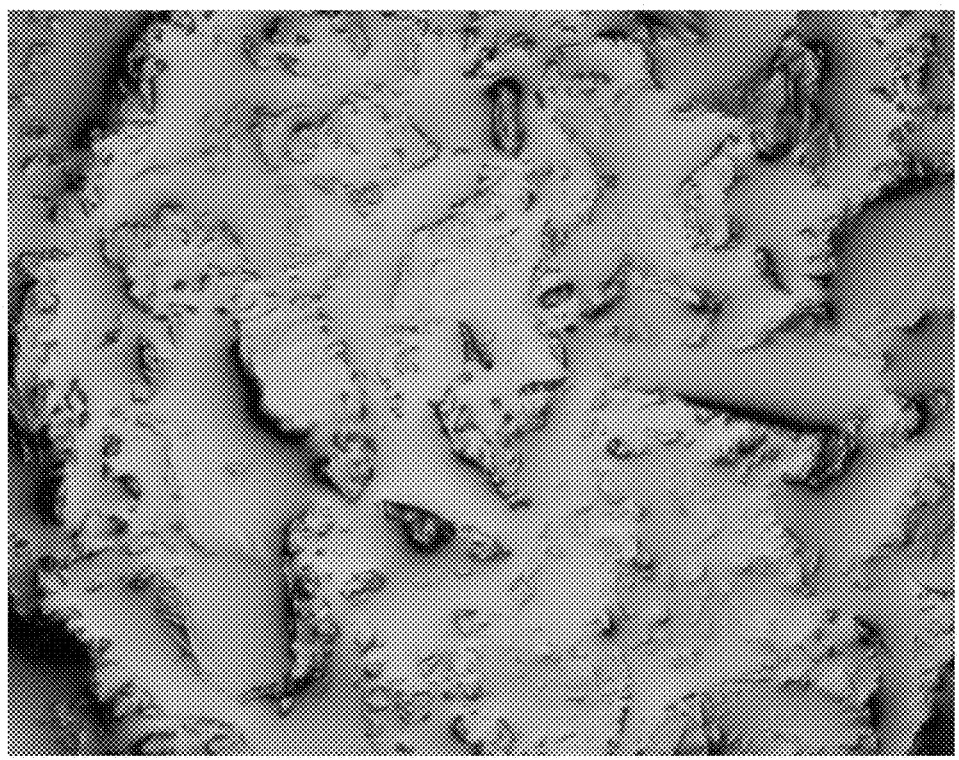
FIG. 6A is an image of film formation of a photoprotective composition
Figure 6B:
FIG. 6B is an image of film formation of a photoprotective composition
Figure 6C:
FIG. 6C is an image of film formation of a photoprotective composition
Figure 6D:
FIG. 6D is an image of film formation of a photoprotective composition
Figure 6E:
FIG. 6E is an image of film formation of a photoprotective composition
Figure 6F:
FIG. 6F is an image of film formation of a photoprotective composition

As shown in FIG. 6A, the untreated Schonberg HD2 PMMA plate is rough with peaks (shown as the sharper and darker areas). In FIGS. 6B and 6D, the CT Sport SPF 50 product and the BANANA BOAT® SPORT SPF 50 product, respectively provides some coverage to the Schonberg HD2 PMMA plate, yet many of the rough peaks still remain and are visible as dark and sharp points. As shown in FIG. 6C, the NEUTROGENA COOLING MIST SPF 45 with KP 545 product provides improved coverage, as the Schonberg HD2 PMMA plate shows fewer roughened peaks. As shown in FIG. 6E, the BANANA BOAT COOL ZONE SPF 50 with ADVANTAGE PLUS product also shows fewer roughened peaks. An advantage of the BANANA BOAT COOL ZONE SPF 50 with ADVANTAGE PLUS over products that use KP 545 such as the NEUTROGENA COOLING MIST SPF 45 is that the ADVANTAGE PLUS is significantly less expensive. As exemplified in FIG. 6F, the exemplary embodiment of the present disclosure with a polymer composition and HMA as in exemplary test embodiment A6 provides the most complete coverage. Almost none, if any, peaks of the Schonberg HD2 PMMA plate are visible or remain uncovered. Furthermore, the film formed appears smooth or soft, further indicating that the film is uniformly applied, particularly in the absence of any viewable rough areas and/or peaks of the Schonberg HD2 PMMA plate. Further still, the exemplary embodiment of the present disclosure utilizes COSMOSURF PG-1-IS, which is also significantly less expensive than the KP 545. As such, the present disclosure has unexpectedly achieved a low-cost alternative that provides significantly improved film formation.

Table 12 below describes other test embodiments and their UVR absorbencies.

TABLE 12

| Ingredients (% w/w)* | B7 | B8 | B9 |
|---|---|---|---|
| Hydrogenated Methyl Abietate | — | 1.00% | 5.00% |
| Polyglyceryl Stearate/Isostearate Dilinoleate Crosspolymer | 5.00% | 5.00% | 1.00% |
| Lauryl PEG-8 Dimethicone | 5.00% | 5.00% | 1.00% |
| Phenylisopropyl Dimethicone | 5.00% | 5.00% | 1.00% |
| in vitro SPF (1 mg/cm² PMMA HD2) | 83 ± 2 | 97 ± 3 | 81 ± 2 |
| in vitro UVA/UVB | 0.737 | 0.744 | 0.731 |
| Labsphere Critical Wavelength (nm) | 376 | 377 | 377 |
| UVA1 (λ nm @0.5 abs) | 390.0 | 391.0 | 391.0 |

*Homosalate 10 wt. %, Octisalate 5 wt. %, Octocrylene 5 wt. %, Avobenzone 3 wt. %

Figure 7A:
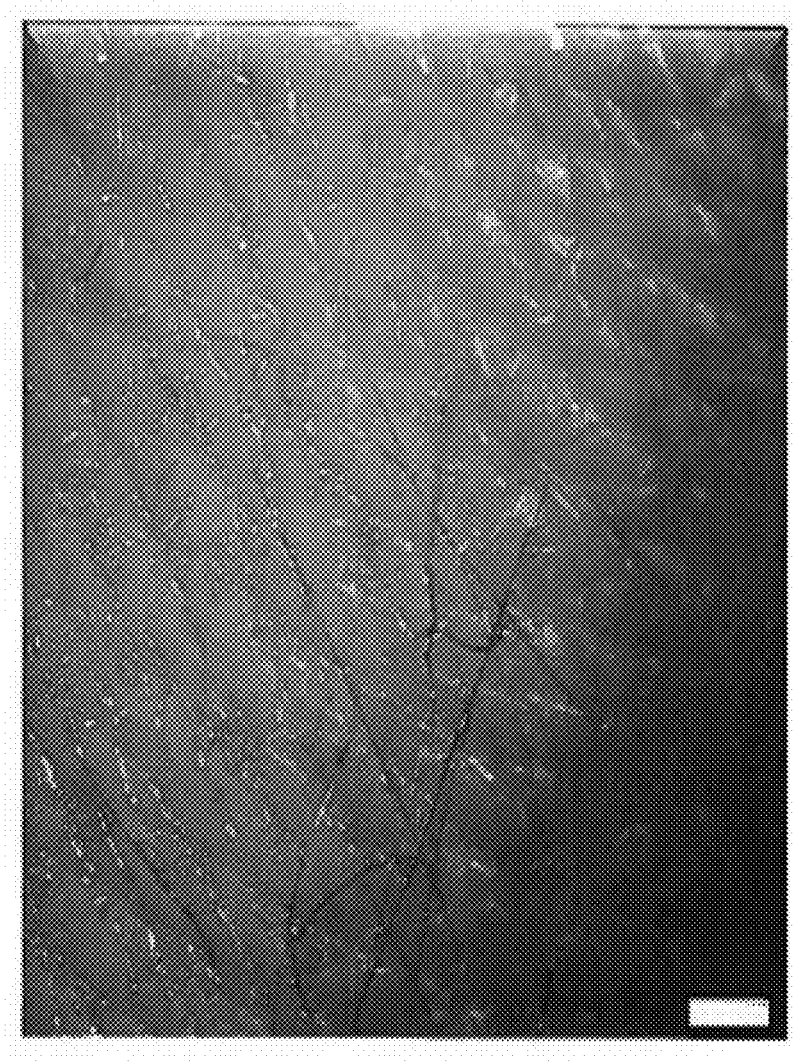
FIG. 7A is an image of film formation of a photoprotective composition

FIGS. 7A-7C demonstrate uniformity and durability of an exemplary embodiment of the present disclosure, as in exemplary test embodiment A6. The exemplary test embodiment A6 was dyed and topically applied to a substrate. Using an OLYMPUS SZX16 Microscope, images described in FIGS. 7A-7C were taken at a 1.6× magnification. One can see untreated substrate in FIG. 7A and treated substrate in FIGS. 7B and 7C. FIG. 7C demonstrates that upon disturbing, rubbing, and/or otherwise moving the substrate, the film of the exemplary embodiment of the present disclosure remains uniformly distributed. In other words, the film of the exemplary embodiment of the present disclosure is durable, as it remains consistently applied after the substrate surface has been moved, touched, rubbed, abraded or otherwise disturbed.

The present disclosure's photoprotective composition is provided such that the composition is a single phase. The photoprotective composition is mixed in one stage (i.e. a single phase) such that multiple phases or stages where certain water, emulsion or oil phases are required in order to obtain a suitable photoprotective composition are unnecessary. As such, the number of steps that are required in manufacturing the photoprotective composition of the present disclosure are reduced.

In another embodiment, the photoprotective composition is homogenous such that the product does not require shaking, agitation, or other physical movement in order to dispense the photoprotective composition from a container such that the photoprotective composition is of a substantially uniform consistency. Homogeneity can be facilitated by embodiments of the present disclosure that are single phase, but homogeneity can be achieved with liquids that are not a single phase.

In one embodiment, the photoprotective composition is substantially non-whitening. The photoprotective composition is substantially non-whitening upon being dispensed from a container such that the photoprotective composition is substantially non-whitening when applied to a substrate. In other words, the photoprotective composition is substantially non-whitening upon removal from a canister, upon topical application, upon a significant length of time passing after topical application, or any combinations thereof. The photoprotective composition may also be substantially non-whitening after being topically applied and having sufficient time to dry. The photoprotective composition may also be substantially non-whitening when applied to substantially wet or substantially dry substrates, or combinations thereof. Said another way, the photoprotective composition is substantially non-whitening when topically applied to a substantially wet substrate, to a substantially dry substrate, or combinations thereof.

A substantially non-whitening composition can be quantified by visual perception studies including the ability to identify/ascertain something lying below/underneath a composition. For instance and for purposes of the present disclosure, a substantially non-whitening liquid is defined by the ability to read font size of 10 point or less printed on a substrate onto which a liquid is applied. Preferably and for the purposes of the present disclosure, a substantially non-whitening liquid visual perception study requires being able to read a font size of 4 to 6 through three (3) inches of liquid. The following scale is exemplary:

This is 10 point font
This is 8 point font
This is 6 point font
This is 4 point font In one embodiment, the photoprotective composition is substantially non-whitening such that 10 point Arial font can be read through three (3) inches of the photoprotective composition liquid. In another embodiment, the photoprotective composition is substantially non-whitening such that 8 point Arial font can be read through three (3) inches of the photoprotective composition liquid. More preferably, in another embodiment, the photoprotective composition is substantially non-whitening such that 6 point Arial font can be read through three (3) inches of the photoprotective composition liquid. Most preferably, an embodiment of the photoprotective composition is substantially non-whitening such that 4 point Arial font can be read through three (3) inches of the photoprotective composition liquid.

Another means of ascertaining of whether or not a liquid is substantially non-whitening is by how the liquid visually appears when applied to a substantially wet substrate, a substantially dry substrate, or combinations thereof. In other words, the liquid should not produce an opaque film upon (a) initial application of the liquid to the substrate, regardless of whether the substrate is wet, dry or combinations thereof, (b) upon being lathered, oscillated, or rubbed onto, over and/or into the substrate, (c) after a sufficient time has passed between either or both of (a) and (b) such that the substrate has had a chance to dry or settle into a finally-applied state on the substrate. In one embodiment, the photoprotective composition does not produce an opaque film upon initial application to a substrate, wherein the substrate is substantially wet, substantially dry, or combinations thereof. In another embodiment, the photoprotective composition does not produce an opaque film upon lathering, oscillation, rubbing onto, over or into the substrate, wherein the substrate is substantially wet, substantially dry, or combinations thereof. In another embodiment, the photoprotective composition does not produce an opaque film after the photoprotective composition has had sufficient time to dry after (a) initial application to a substantially wet substrate, a substantially dry substrate, or combinations thereof, (b) lathering, oscillation or rubbing onto, over and into a substantially wet substrate, a substantially dry substrate, or combinations thereof, or both (a) and (b). In a preferred embodiment, the photoprotective composition never leaves an opaque film upon application to a substantially wet substrate, a substantially dry substrate, or combinations thereof.

In one embodiment, the present disclosure's photoprotective composition is substantially non-irritating. In one embodiment, the present disclosure's photoprotective composition is substantially non-irritating in that it is mild, or in other words, it elicits substantially no dermal irritation, such as but not limited to, i.e., sensitization, erythema, stinging, burning, itching, eczema, flaking, drying, other skin conditions and combinations thereof. In other words, the photoprotective composition is substantially non-irritating such that upon topical application, minimal dermal irritation is elicited.

In another embodiment, the present disclosure's photoprotective composition is substantially non-irritating in that it is mild, or in other words, it elicits substantially no ocular irritation, such as but not limited to, i.e., non-lacrimating (non-tearing, tear-free); does not induce stinging, burning, or itching; does not induce ocular, bulbar conjunctival irritation, palpebral conjunctival irritation, or any combinations thereof. In other words, the photoprotective composition is substantially non-irritating such that upon topical application, minimal ocular irritation is elicited.

In another embodiment, a photoprotective composition is substantially non-whitening and is also substantially non-irritating. In some of these embodiments, the photoprotective composition is substantially non-whitening on a substantially dry substrate. In other of these embodiments, the photoprotective composition may be substantially non-whitening on a substantially wet substrate. In other embodiments, the photoprotective composition may be substantially non-whitening on a substantially wet substrate and a substantially dry substrate. In some of these embodiments, the photoprotective composition is substantially non-whitening upon dispensing from a container and upon application to a substrate. In further embodiments, the photoprotective composition is also substantially non-whitening after a sufficient amount of time has elapsed in order to permit the photoprotective composition to dry onto, over and/or into the substrate. In yet further embodiments, the photoprotective composition are substantially non-whitening upon being rubbed, lathered, and oscillated onto, over and/or into the substrate. Preferably, the photoprotective composition of these embodiments is completely non-whitening. In any of these embodiments and as noted above, the photoprotective composition may also be substantially non-irritating such that is causes substantially no dermal irritation. In any of these embodiments, the photoprotective composition may also be substantially non-irritating in that it causes substantially no ocular irritation. In further embodiments, the photoprotective composition may also be substantially non-irritating in that it causes substantially no ocular lacrimation, substantially no ocular sting, or both. In yet further embodiments, the photoprotective composition is preferably non-irritating. In yet further embodiments, the photoprotective composition preferably causes no ocular lacrimation, causes no ocular sting, causes no dermal irritation, or any combinations thereof. In further embodiments, the photoprotective composition may also be homogenous, a single phase, anhydrous, water-resistant, or any combinations thereof. One skilled in the art appreciates how surprising and unexpected achieving a photoprotective composition with any single characteristic as described throughout is. One skilled in the art truly appreciates the challenge in balancing any number or plurality of characteristics as described throughout, while still maintaining a sufficient level of photoprotection. One skilled in the art has further appreciation for the challenges of accomplishing a photoprotective composition that is, for instance, non-irritating and/or non-whitening, may further be a single phase and/or is homogenous and/or anhydrous, and achieving this without (i.e., such that the photoprotective composition is substantially free of) alcohol, preservatives, further active ingredients (i.e., oxybenzone), surfactants, other chemicals, or any combinations thereof.

While embodiments of the photoprotective composition do not necessitate the following, other ingredients can include, but are not limited to, i.e., water, solvents, emollients, emulsifiers, skin protectants such as dimethicone specified in the FDA Skin Protectant Drug Products for Over-The-Counter Human Use, 21 C.F.R. §§ 310, 347, 352, additional film forming and/or water proofing agents, preservatives, SPF boosters, vitamins and/or antioxidants, silicones, and silicone derivatives, thickening agents, moisturizers, humectants, bio-actives, pH adjuster/chelating agents, preservatives, fragrances, effect pigments, color additives, lubricants, elastomers, and any combinations thereof.

In one embodiment, at least one preservative is included in the photoprotective composition. Preferably, a small amount of at least one preservative may be included in order to account for inadvertent contamination, such as when a consumer opens and closes a container holding photoprotective composition therein. Upon opening, microbial contamination can occur. In other words, although at least one preservative may be prove beneficial, the present disclosure provides for embodiments that do not require preservatives and thus are not so limited to comprising preservatives.

In one embodiment, an emulsifier is selected from the group comprising lauryl PEG-8 dimethicone, cetyl PEF/PPG-10/1 dimethicone, sodium lauroyl sarcosinate, caprylyl glycol, ethylhexyl methoxycrylene, butyloctyl salicylate, and any combinations thereof.

In another embodiment, a silicone is selected from the group comprising dimethicone, cyclopentasiloxane, cyclohexasiloxane, ethyl methicone, ethyl trisiloxane, polysilicone-15, cetyl dimethicone/bis-vinyl-dimethicone cross polymer, polymethylsilsesquioxane, and any combinations thereof.

In yet another embodiment, a further film former/waterproofing agent is selected from the group comprising mineral oil, lotus japonicas symbiosome extract, $C_{14}$ to $C_{22}$ alkanes, $C_{13}$ to $C_{16}$ isoparaffins, $C_{12}$ to $C_{14}$ isoparaffins, $C_{13}$ to $C_{15}$ alkanes, polyester-25, polyester-10, propylene glycol dibenzoate, polyester-7, neopentyl glycol diheptanoate, polyester-17, trimethylsiloxy silicate, VA/butyl maleate/isopropyl acrylate copolymer, acrylates/dimethicone copolymer, cyclomethicone, acrylates/octylacrylamide copolymer, and combinations thereof.

Additionally, in yet further embodiments, further ingredients can be added such as but not limited to, i.e., cetyl PEG/PPG-10/1 dimethicone (trade name ABIL® EM-90), caprylyl glycol (trade name JEECIDE® CAP), ethylhexyl methoxycrylene (trade name SOLASTAY® S1), butyloctyl salicylate (trade name HALLBRITE® BHB), 1,3 butylene glycol, methylparaben, propylparaben, phenoxyethanol (trade name JEECIDE® Phenoxy), ethanol, propylene glycol, diazolidinyl urea, iodopropoynyl butylcarbamate (trade name LIQUID GERMALL PLUS), phenoxyethanol, methylparaben, butylparaben, ethylparaben, propylparaben (trade name PHENONIP®), dimethicone (trade name DOW CORNING® 200 Fluid 50 CST), cyclopentasiloxane and cyclohexasiloxane (also known as cyclomethicone; (trade name XIAMETER® PMX-0345), ethyl methicone (trade name SILWAX® D-02), ethyl trisiloxane (trade name SILSOFT® ETS), polysilicone-15 (PARSOL® SLX), cetyl dimethicone/bis-vinyl-dimethicone crosspolymer (trade name SILWAX® CR5016), polymethylsilsesquioxane (trade name MST-547), cetyl dimethicone (trade name ABIL® Wax 9801), phenyl trimethicone, stearyl dimethicone, PEG-8 (trade name CARBOWAX® PEG-400), glycerin (trade name Emery 917), Ozokerite Wax, hydrogenated castor oil (trade name CASTORWAX® MP 70), paraffin wax, polyethylene, microcrystalline wax, octododecyl citrate crosspolymer (trade name COSMOSURF® CE-100), cetearyl ethylhexanoate (trade name SCHERCEMOL 1688), glyceryl stearate, behenyl alcohol, palmitic acid, stearic acid, lecithin, lauryl alcohol, myristyl alcohol and cetyl alcohol known such as by the trade name PROLIPID® 141, stearic acid (trade name EMERSOL® 132), polyoxyethylene (20) stearyl ether (trade name BRIJ® 78), PPG-20, methyl glucose ethers such as those sold under the trade names GLUCAM® E-20 or GLUCAM P-20, cetyl PEG/PPG 111 Dimethicone (trade name ABIL EM-90), squalane (trade name FITODERM), cetyl alcohol, carbomer (trade name CARBOPOL® Ultrez-10), fragrance, water, disodium EDTA, sodium chloride, magnesium sulfate, sodium ascorbyl phosphate, ascorbyl palmitate, triethanolamine, sodium citrate, and combinations thereof.

One skilled in the art that the application is not so limited by the trade names provided throughout the present disclosure and that components, chemicals, materials, additives, constituents and any other ingredient can be of similar composition to those listed and can be sourced from other products by different trade names or brands than those noted throughout the present disclosure.

In one aspect of the present disclosure, the photoprotective composition may be easier to manufacture. The key components of the photoprotective composition of the present disclosure inherently possess oil solubility (i.e., are lipophilic) and many embodiments of the present disclosure are also anhydrous. In other words, the constituents of the photoprotective compositions of the present disclosure may be amphipathic. As such, embodiments of the present disclosure can be manufactured at ambient conditions and thus don't require elevated temperatures for manufacture. In some embodiments, heat may optionally be applied in order to reduce processing time, but increased temperature or heat is not necessary otherwise. In other embodiments of the present disclosure, manufacturing can be shortened from a time standpoint if solid ingredients (i.e., avobenzone, bemotrizinol, waxes, and other ingredients that are substantially solid at room temperature) are mixed with liquids and then heated to melt temperature. Adding liquids may also be used to cool the batch quickly, and as such, one skilled in the art that the photoprotective compositions of the present disclosure can provide fewer processing steps, fewer processing constraints (i.e. ambient temperature may be sufficient), and combinations thereof.

In various embodiments, the photoprotective composition can be filled into any number of bottles, tottles, tubes having a variety of closing means, pumps, sprays (i.e., aerosols, bag on valve), amongst others, and combinations thereof. Aerosol embodiments can be filled with various propellants and combinations of propellants, depending on requirements for that product. Propellants that may be used include but are not limited to, i.e., isobutene, isobutene/propane, dimethyl ether, tetraflouroethane, and 1,1-difluoroethane. Ratios of propellant to the photoprotective composition concentrate can be adjusted to account for cost, aesthetics, and product performance objectives.

In one embodiment of the present disclosure, alcohol is not necessary. Alcohols often elicit dermal and/or ocular irritation (i.e., stinging and/or burning) and as such, are not required for purposes of the present disclosure. One of skill in the art understands that alcohols may be included, but they are likewise not required, nor is the present disclosure so limited to including alcohol. In view of the absence of alcohol, embodiments of the present disclosure may be more suitable for sprays including both aerosol and bag on valve systems. Embodiments without alcohol are potentially less-flammable than formulations containing alcohol.

In one embodiment, at least one propellant may be used such as, but not limited to, i.e., isobutene, propane, dimethyl ether, tetraflouroethane, 1,1-difluoroethane, and combinations thereof.

In one embodiment, the photoprotective composition concentrate and propellant are added to an aerosol container in a ratio of about 70:30 to about 60:40. The tetraflouroethane and difluoroethane propellants were tested and are non-flammable in view of the flame extension test.

In another embodiment, the photoprotective composition concentrate and propellant are added to an aerosol container in a ratio of about 70:30. The tetraflouroethane and isobutene propellants were evaluated to determine what blends of tetraflouroethane and isobutene propellants would provide a non-flammable product at a reasonable cost. In other words, it was found that a lowest ratio of tetraflouroethane to isobutene propellant that achieved no flame extension was a ratio of about 3:1. In some embodiments having a photoprotective composition comprising a concentrate and at least one propellant, the ratio of the photoprotective composition and the propellant can be between about 2.5:1 and about 1.25:1.

In order to evaluate overall performance of photoprotective compositions of the present disclosure, sensory and consumer testing can be done and benchmarked against existing products. In one such in-house study with between seven (7) and ten (10) panelists, several embodiments of the photoprotective compositions of the present disclosure were tested, including two compositions containing high levels of isohexadecane (73.4 wt. % and 74.98 wt. %) and two different silicone blends (cyclopentasiloxane/cyclohexasiloxane, polymethylsilsesquioxane/ethylmethicone), which were compared to a control of the currently sold BANANA BOAT SPORT Lotion Spray that claims to be tear-free and sting-free. The aforementioned embodiments of the present disclosure's photoprotective compositions were substantially non-whitening upon application and upon being rubbed-in; the currently sold BANANA BOAT SPORT Lotion Spray currently sold was found to whiten upon being rubbed-in. Feedback from the ten (10) panelists noted the embodiments of the present disclosure's photoprotective compositions that were tested were significantly shinier, greasier and/or oily on the skin. All three compositions tested contained isobutene propellant.

In a second in-house study with between seven (7) and ten (10) panelists, different embodiments of the present disclosure's photoprotective composition were tested: an embodiment comprised 37.68 wt. % isohexadecane, 34.00 wt. % ethylhexyl palmitate and cyclopentasiloxane/cyclohexasiloxane. The ratio of concentrate to propellant was 60:40; the propellants evaluated were isobutene and dimethyl ether. The control product was once again the currently sold BANANA BOAT SPORT Lotion Spray. Upon applying to dry skin, the embodiment comprising dimethyl ether was surprisingly found to be significantly shinier and more oily and/or greasier than the embodiment comprising dimethyl ether. When applied to wet skin, the currently sold BANANA BOAT SPORT Lotion Spray was more difficult to rub-in and/or spread, and furthermore, whitened the skin. Surprisingly, the embodiments of the present disclosure were found to be easy to rub-in and/or spread, and were substantially non-whitening. As such, in one embodiment, it may be preferable to have a concentrate to propellant ratio of 60:40, wherein the propellant is at least partially comprised of dimethyl ether. While this embodiment may provide, upon application, a product that is less shiny, less greasy and/or less oily, one of skill in the art understands that all exemplary embodiments of the present disclosure's photoprotective compositions demonstrate substantially non-whitening products.

In another study, sixty (60) consumers were provided embodiments of the photoprotective compositions of the present disclosure for home-use. One embodiment comprised 20 wt. % isohexadecane, 54.1 wt. % ethylhexyl palmitate, and no siloxanes. The concentrate to propellant ratio of this embodiment tested was 60:40, and the propellant evaluated was dimethyl ether. The control product was the currently sold BANANA BOAT SPF 50 Kids bag-on-valve product. So as to prevent fragrance halo effects, fragrance was added to the test embodiment. Results from the study showed test embodiment of the photoprotective composition of the present disclosure was preferred based on the following characteristics/factors:

Overall liking: Preferred at 80% confidence limit (CL)

Skin feel, liking rubbing-in: Preferred at 90% CL

Did not feel sticky or tacky: Preferred at 90% CL

Did not turn white when sprayed on wet skin: Preferred at 90% CL

Skin feel softness: Preferred at 80% CL

Skin feel smoothness: Preferred at 90% CL

As such, one skilled in the art understands that the above-mentioned tested embodiments demonstrate the photoprotective composition of the present disclosure provide a significantly improved consumer experience, as identified in the above-mentioned sensory characteristics/factors. One skilled in the art further understands that the present disclosure has unexpectedly achieved a photoprotective composition that provides for one or more of these sensory characteristics/factors, one or more of the physical attributes and/or characteristics that provides for the sensory results shown above, and that a plurality of embodiments, as demonstrated above and throughout the present disclosure can achieve the desired performance criteria acknowledged throughout the present disclosure.

Although the present disclosure has been described and illustrated with reference to specific exemplary embodiments thereof, it is not intended that the invention be limited to those exemplary embodiments. Those skilled in the art will recognize that variations and modifications can be made without departing from the true scope of the present disclosure as defined by the claims that follow. For instance, features disclosed in connection with any one embodiment can be used alone or in combination with each feature of the respective other embodiments.

What is claimed is:

1. A photoprotective composition, comprising:
   at least one photoactive agent present in an amount of about 0.1 to about 40 wt. %, based on a total weight of the photoprotective composition;
   a synergistic combination of polymers present in an amount of about 0.1 to about 15 wt. %, based on a total weight of the photoprotective composition comprising:
      0.1 to 5 wt. % of an alkyl-dimethicone having a hydrophilic group, an alkyl-PPG dimethicone, an alkyl-PEG dimethicone, or combinations thereof;
      0.1 to 5 wt. % of a polymer with ester linkages comprising polyglyceryl stearate/isostearate dilinoleate crosspolymer in semi-solid form, polyglyceryl stearate/isostearate dilinoleate crosspolymer in liquid form, polyglyceryl stearate/isostearate dilinoleate crosspolymer in solid form or combinations thereof; and
      0.1 to 5 wt. % of phenylisopropyl dimethicone; and
      0.1 to 5 wt. % of an abietic acid ester,
   wherein said photoprotective composition is an anhydrous, single phase, homogenous composition that forms a substantially complete film on a dry or wet substrate, and wherein said synergistic combination of polymers increases a UVR absorbance of the photoprotective composition in comparison with a photoprotective composition without said synergistic combination of polymers.

2. The photoprotective composition of claim 1, wherein said at least one photoactive agent is selected from the group consisting of p-aminobenzoic acid and derivatives thereof, butyl methoxydibenzoylmethane, benzophenones, hydroxy-substituted benzophenones, methoxy-substituted benzophenones, benzophonone-1, benzophenone-2, benzophenone-3, benzophenone-4, benzophenone-6, benzophenone-8, benzophenone-12, methoxycinnamate, ethyl dihdroxypropyl-p-aminobenzoate, glyceryl-p-aminobenzoate, homosalate, methyl anthranilate, octocrylene, octyl dimethyl-p-aminobenzoate, octyl methoxycinnamate, octyl salicylate, 2 phenylbenzimidazole-5-sulphonic acid, triethanolamine salicylate, 3-(4-methylbenzylidene)-camphor, red petrolatum,3-(4-methylbenzyldine)boran-2-one (methylbenzindinecamphor), benzotriazole, phenylbenzimidazole-5-sulfonic acid, methylene bis-benzotriazolyl tetramethylbutyl phenol, 4-isopropyldibenzoymethane, octocrylene, octisalate, oxybenzone, bis-ethylhexyloxyphenol methoxy triazine, 4-isopropyl-dibenzoylmethane, metal oxides, zinc oxide, octyltriethoxy silanol, titanium dioxide, alumina, triethoxysilane, and any combinations thereof.

3. The photoprotective composition of claim 1, wherein said alkyl dimethicone comprises lauryl PEG-8 dimethicone.

4. The photoprotective composition of claim 1, wherein said at least one photoactive agents comprises: homosalate in an amount less than or equal to 15 wt. %, octisalate in an amount less than or equal to 5 wt. %, octocrylene in an amount less than or equal to 10 wt. %, avobenzone in an amount less than or equal to 5 wt. %, oxybenzone in an amount less than or equal to 0.5 wt. %, and bis-ethylhexyloxyphenol methoxyphenyl triazine in an amount less than or equal to 2.0 wt. %, based on a total weight of the photoprotective composition.

5. The photoprotective composition of claim 1, wherein said photoprotective composition further comprises an abietic acid or ester derivative comprising hydrogenated methyl abietate, hydrogenated glyceryl abietate, or a combination thereof.

6. The photoprotective composition of claim 5, wherein said abietic acid and ester derivatives is present in an amount of 0.1 to 1.5 wt. %, based on a total weight of the photoprotective composition.

7. The photoprotective composition of claim 1, wherein said alkyl dimethicone is present in an amount of 0.1 to 1.5 wt. %, based on a total weight of the photoprotective composition.

8. The photoprotective composition of claim 1, wherein said polymer with ester linkages is present in an amount of 0.1 to 1.5 wt. %, based on the total weight of the photoprotective composition.

9. The photoprotective composition of claim 1, wherein said phenyl silicone is present in an amount of 0.1 to 1.5 wt. %, based on a total weight of the photoprotective composition.

10. The photoprotective composition of claim 1 further comprising one or more components selected from the group consisting of solvent, emulsifier, silicone, thickening agent, emollient, SPF booster, moisturizer, humectant, film former/waterproofing agent, bio-active, pH adjuster/chelating agent, preservative, fragrance, effect pigment, color additive, lubricant, elastomer, antioxidant, vitamin, and any combinations thereof.

11. The photoprotective composition of claim 1, further including an emulsifier selected from the group consisting of cetyl PEG/PPG-10/1 dimethicone, sodium lauroyl sarcosinate, and any combinations thereof.

12. The photoprotective composition of claim 11, wherein said photoprotective composition comprises a concentrate and at least one propellant, wherein the ratio of said photoprotective composition and said propellant is between about 2.5:1 and about 1.25:1.

13. The photoprotective composition of claim 1 further comprising at least one propellant, wherein said at least one propellant is selected from the group consisting of: isobutene, propane, dimethyl ether, tetrafluoroethane, 1,1-difluoroethane, and combinations thereof.

14. The photoprotective composition of claim 1, wherein said photoprotective composition provides a critical wavelength of greater than or equal to 390 nm as measured using the 2011 FDA Final Rule for Very Water Resistance.

15. The photoprotective composition of claim 1, wherein said photoprotective composition is substantially free of preservatives, is substantially free of surfactants, is substantially free of alcohol, is substantially free of emulsifiers, is a skin-protectant, or any combinations thereof.

16. A photoprotective composition, comprising:
   at least one photoactive agent in an amount of about 0.1 wt. % to about 40 wt. %; and
   a synergistic combination of polymers comprising:
      lauryl PEG-8 dimethicone in an amount of about 0.1 wt. % to about 1.5 wt. %;
      polyglyceryl-3 stearate/isostearate dilinoleate crosspolymer in an amount of about 0.1 wt. % to about 1.5 wt. %; and
      phenylisopropyl dimethicone in an amount of about 0.1 wt. % to about 1.5 wt. %; and
      hydrogenated methyl abietate or hydrogenated glyceryl abietate in an amount 0.1 wt. % to 1.5 wt. %,
   wherein said photoprotective composition is an anhydrous, single phase, homogenous composition that forms a substantially complete film on a dry or wet substrate, and wherein said synergistic combination of polymers increases a UVR absorbance of the photoprotective composition in comparison with a photoprotective composition without said synergistic combination of polymers.

17. The photoprotective composition of claim 16 wherein the at least one photoactive agent comprises homosalate, octisalate, octocrylene, avobenzone, or combinations thereof.

18. The photoprotective composition of claim 17 wherein the synergistic combination of polymers comprises lauryl PEG-8 dimethicone, polyglyceryl-3 stearate/isostearate dilinoleate crosspolymer, phenylisopropyl dimethicone, or combinations thereof.

* * * * *